(12) United States Patent
Lebkowski et al.

(10) Patent No.: US 9,074,182 B2
(45) Date of Patent: *Jul. 7, 2015

(54) DIFFERENTIATED PLURIPOTENT STEM CELL PROGENY DEPLETED OF EXTRANEOUS PHENOTYPES

(71) Applicant: Asterias Biotherapeutics, Inc., Menlo Park, CA (US)

(72) Inventors: Jane S. Lebkowski, Portola Valley, CA (US); Catherine Ann Priest, San Carlos, CA (US); Ross M. Okamura, Menlo Park, CA (US)

(73) Assignee: Asterias Biotherapeutics, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/679,663

(22) Filed: Nov. 16, 2012

(65) Prior Publication Data
US 2013/0210109 A1    Aug. 15, 2013

Related U.S. Application Data

(63) Continuation of application No. 12/823,739, filed on Jun. 25, 2010, now Pat. No. 8,323,966.

(60) Provisional application No. 61/220,418, filed on Jun. 25, 2009.

(51) Int. Cl.
C12N 5/074 (2010.01)
C12N 5/0797 (2010.01)

(52) U.S. Cl.
CPC ............ *C12N 5/0607* (2013.01); *C12N 5/0623* (2013.01); *C12N 2506/02* (2013.01)

(58) Field of Classification Search
CPC . C12N 5/0623; C12N 5/0607; C12N 2506/02
See application file for complete search history.

(56) References Cited

U.S. PATENT DOCUMENTS

| | | |
|---|---|---|
| 6,458,589 B1 | 10/2002 | Rambhatla et al. |
| 6,506,574 B1 | 1/2003 | Rambhatla et al. |
| 6,833,269 B2 | 12/2004 | Carpenter |
| 7,033,831 B2 | 4/2006 | Fisk et al. |
| 7,256,042 B2 | 8/2007 | Carpenter et al. |
| 7,285,415 B2 | 10/2007 | Keirstead et al. |
| 7,326,572 B2 | 2/2008 | Fisk et al. |
| 7,425,448 B2 | 9/2008 | Xu |
| 7,452,718 B2 | 11/2008 | Gold et al. |
| 7,473,555 B2 | 1/2009 | Mandalam et al. |
| 7,993,916 B2 | 8/2011 | Agulnick et al. |
| 8,323,966 B2 * | 12/2012 | Lebkowski et al. ........... 435/368 |
| 2004/0009593 A1 | 1/2004 | Keirstead et al. |
| 2004/0224403 A1 | 11/2004 | Bhatia |
| 2005/0095708 A1 | 5/2005 | Pera et al. |
| 2005/0158855 A1 | 7/2005 | Carpenter et al. |
| 2005/0282272 A1 | 12/2005 | Bhatia et al. |
| 2005/0282274 A1 | 12/2005 | Xu et al. |
| 2006/0040389 A1 | 2/2006 | Murry et al. |
| 2006/0148077 A1 | 7/2006 | Thies |
| 2007/0274970 A1 | 11/2007 | Gordon et al. |
| 2008/0206343 A1 | 8/2008 | Edinger et al. |
| 2009/0246869 A1 | 10/2009 | Tseng et al. |

FOREIGN PATENT DOCUMENTS

| | | |
|---|---|---|
| WO | WO-2005/097980 | 10/2005 |
| WO | WO-2007/149182 | 12/2007 |

OTHER PUBLICATIONS

Carpenter, M. et al., "Enrichment of neirons and neural precursors from human embryonic stem cells", *Exp. Neurol.* 172(2), (2001),pp. 383-397.

Chadwick, K. et al., "Cytokines and BMP-4 promote hematopoietic differentiation of human embryonic stem cells", *Blood* 102(3), (2003),pp. 906-915.

Invitrogen, *Invitrogen/Dynal*, Invitrogen Catalog No. 161.02 REv. No. 4, *Dynabeads Epithelial Enrich*, (2006),2 pages.

Jiang, J. et al., "Generation of insulin-producing islet-like clusters from human embryonic stem cells", *Stem Cells* 25(8), (2007),pp. 1940-1953.

Keirstead, H. et al., "Human embryonic stem cell-derived oligodendrocyte progenitor cell transplants remyelinate and restore locomotion after spinal cord injury", *J. Neurosci.* 25(19), (2005),pp. 4694-4705.

Laflamme, M. et al., "Cardiomyocytes derived from human embryonic stem cells in pro-survival factors enhance function of infarcted rat hearts", *Nature Biotechnol.* 25, (2007),pp. 1015-1024.

Li, J-Y. et al., "Critical issued of clinical human embryonic stem cell therapy for brain repair", *Trends Neurosci.* 31(3), (2008),pp. 146-153.

Sundberg, M. et al., "CD marker expression profiles of human embryonic stem cells and their neural derivatives, determined using flow-cytometric analysis, reveal a novel CD marker for exclusion of pluripotent stem cells", *Stem Cell Res.* 2(2), (2009),pp. 113-124.

* cited by examiner

*Primary Examiner* — Doug Schultz
(74) *Attorney, Agent, or Firm* — Law Office of Salvatore Arrigo and Scott Lee, LLP

(57) ABSTRACT

The invention provides methods for depleting extraneous phenotypes from a mixed population of cells comprising the in vitro differentiated progeny of primate pluripotent stem cells. The invention also provides mixed cell populations enriched for a target cell phenotype where the mixed cell population comprises the differentiated in vitro progeny of primate embryonic stem cells.

7 Claims, 13 Drawing Sheets

Figure 1: Identification of Epithelial Cells in the Spinal Cord

- Clustered epithelial structures were observed in the spinal cord of a small number of rats after transplantation of oligodendroglial progenitors differentiated in vitro from hES cells
- Identified as epithelial cells by typical histomorphology Figure 2: Pan-Cytokeratin (AE1/AE3) Antibody Figure 3: Ber-EP4 EpCAM Antibody Figure 5: Ber-EP4 EpCAM Antibody
Clustered Epithelial Structures in Rat Spinal Cord After Administration of oligodendroglial progenitors differentiated in vitro from hES cells Figure 6: Pan-Cytokeratin (AE1/AE3) Antibody and Ber-EP4 EpCAM Antibody Epithelial Cystic Structures in Rat Spinal Cord After Administration of oligodendroglial progenitors differentiated in vitro from hES cells Figure 7: Pan-Cytokeratin (AE1/AE3) Antibody and Ber-EP4 EpCAM Antibody Clustered Epithelial Structures in Rat Spinal Cord After Administration of oligodendroglial progenitors differentiated in vitro from hES cells Figure 8: Pan-Cytokeratin (AE1/AE3) Antibody and Ber-EP4 EpCAM Antibody Clustered Epithelial Structures in Rat Spinal Cord After Administration of oligodendroglial progenitors differentiated in vitro from hES cells Animal #4377

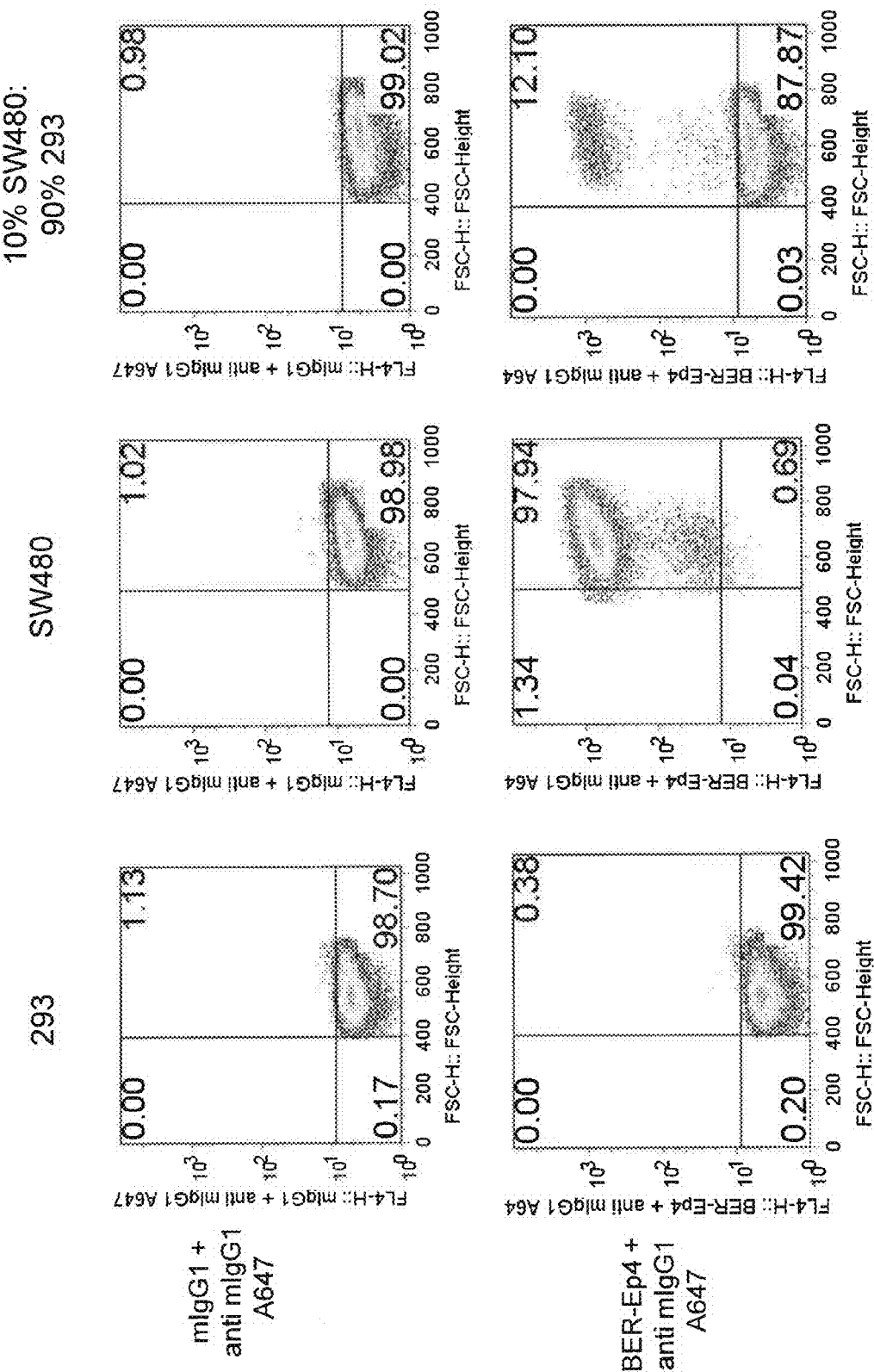

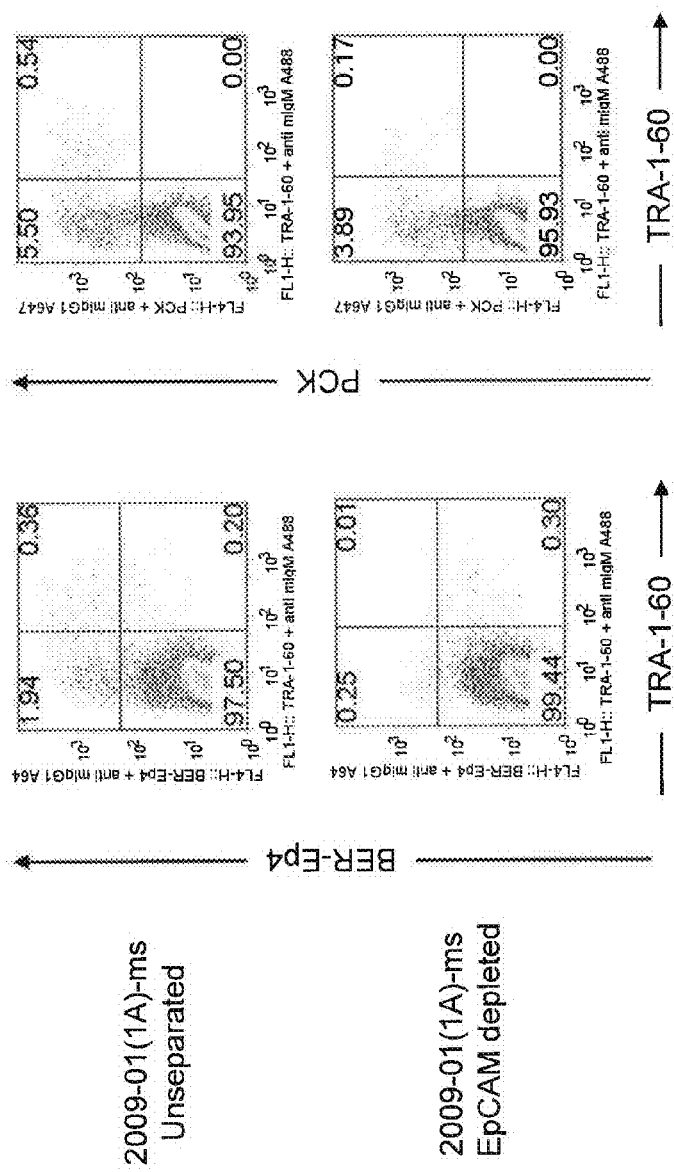
Fig. 11: Directly conjugated anti EpCAM beads successfully remove both TRA-1-60+ and PCK+ cells

DIFFERENTIATED PLURIPOTENT STEM CELL PROGENY DEPLETED OF EXTRANEOUS PHENOTYPES

PRIORITY

This application claims priority to provisional application No. 61/220,418, filed Jun. 25, 2009.

FIELD OF THE INVENTION

The invention relates to the field of stem cell biology.

BACKGROUND

Pluripotent stem cells have the ability to both proliferate in culture and, under appropriate growth conditions, differentiate into lineage restricted cell types representative of all three primary germ layers: endoderm, mesoderm and ectoderm (U.S. Pat. Nos. 5,843,780; 6,200,806; 7,029,913; Shamblott et al., (1998) *Proc. Natl. Acad. Sci. USA* 95:13726; Takahashi et al., (2007) *Cell* 131(5):861; Yu et al., (2007) *Science* 318: 5858). Defining appropriate growth conditions for particular lineage restricted cell types will provide virtually an unlimited supply of that cell type for use in research and therapeutic applications.

Protocols for differentiating primate pluripotent stem (pPS) cells into a variety of targeted cell types including oligodendrocytes, neuronal cells, cardiomyocytes, hematopoietic cells, pancreatic islet cells, hepatocytes, osteoblast and chondrocytes have been described (see, e.g., U.S. Pat. Nos. 7,285,415; 6,833,269; 7,425,448; 7,452,718; 7,033,831; 7,326,572; 6,458,589; 6,506,574; 7,256,042; 7,473,555; U.S. Patent Publication Nos. 2005/0158855; 2004/0224403; 2005/0282272; 2005/0282274; 2006/0148077; U.S. patent application Ser. No. 12/412,183; PCT Publication No. WO 07/149,182; WO 05/097980; Carpenter et al. (2001) *Exp Neurology* 172:383; Chadwick et al. (2003) *Blood* 102:906; Kierstad et al. (2005) *J Neuroscience* 25:4694); Laflamme et al. (2007) *Nature Biotechnology* 25:1015 Jiang et al. (2007) *Stem Cells* 25:1940.

Differentiation of pPS cells into a target phenotype cell may result in production of a mixed population of cells comprising the targeted phenotype as well as various extraneous phenotypes. Certain extraneous phenotypes that retain the pluripotent potential of undifferentiated embryonic stem cells may form teratomas when administered to a subject, see, e.g., Thomson 1998 *Science* 282:1145. Other extraneous phenotypes may interfere with the efficacy of the target phenotype merely by diluting the number of cells of the targeted phenotype thereby reducing the overall efficacy of the cell preparation. Accordingly, there is a need to reduce the number of cells having an extraneous phenotype found in a population of cells comprising the targeted differentiated progeny of pPS cells. There is an additional need for populations of differentiated progeny of pPS cells that have a minimal number of cells of an extraneous phenotype for use in therapeutic, diagnostic and/or research applications. Various embodiments of the invention described herein meet these needs and other needs as well.

SUMMARY OF THE INVENTION

In some embodiments the invention provides a population of cells comprising the in vitro differentiated progeny of pPS cells that is essentially free of extraneous phenotypic cell types. The in vitro differentiated progeny of pPS cells may include target phenotypes chosen from oligodendrocytes, cardiomyocytes, islet cells, hepatocytes, hematopoietic cells, chondrocytes and osteoblasts. One example of extraneous phenotypic cells is an epithelial lineage cell, i.e. a cell expressing one or more markers associated with epithelial cells, such as one or more of the following markers: cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin). These cells may be capable of forming clustered epithelial structures when implanted in a subject such as a rodent Cell populations that are essentially free of extraneous phenotypic cell types may be obtained by screening for markers associated with epithelial cells such as one or more of the following markers: desmocollin 3; desmoglein 2; E-cadherin CD49f, EMA, E-cad, CD321 (Jam1), CD10, CD66, and CD105 (endoglin) cytokeratin. For example an antibody to any one or more of these markers may be used.

In other embodiments the invention provides a method of obtaining a population of cells comprising the in vitro differentiated progeny of pPS cells that is essentially free of extraneous phenotypic cells comprising a) obtaining a population of cells comprising the in vitro differentiated progeny of pPS cells; b) contacting the cell population of a) with one or more ligands that bind to epithelial cells and c) removing the ligand bound cells of b) thereby obtaining a population of cells that is essentially free of extraneous phenotypic cells. Removing the ligand bound cell can include physically separating the ligand bound cell from the rest of cell population. Removing the ligand bound cell may also include killing the ligand bound cell. For example an agent such as toxin that binds to the ligand bound to the cell may used. In one embodiment the ligand may be antibody and complement may be used as agent that lyses the cell and thus removes it from the population of cells.

In certain other embodiments the invention provides for a mixed population of cells comprising the in vitro differentiated progeny of primate pluripotent stem cells. The mixed population of cells may include a targeted phenotypic cell population that is enriched by reducing the number of extraneous phenotypic cells from the mixed population of cells thus providing a more suitable population of cells for use as a therapeutic or research product when compared to a mixed population of cells that has not been reduced in the number of extraneous phenotypic cells. Enrichment of the targeted population of cells is achieved by reducing the number of cells that express specific markers associated with cells of extraneous phenotype, e.g. one or more markers expressed by an epithelial cell. Removal of the extraneous phenotype may include physically separating the extraneous phenotype from other cells comprising the population. Removal of the extraneous phenotype may also include chemically treating the extraneous phenotype to kill the ligand bound cell e.g. a chemical agent that specifically binds to a ligand bound to an extraneous phenotypic cell.

Surprisingly, expression of at least one or more markers associated with extraneous phenotypic cells of epithelial lineage overlaps with expression of at least one or more markers associated with undifferentiated cells, e.g. TRA-1-60. Thus by depleting cells expressing the markers associated with extraneous phenotypes of epithelial lineage the number of undifferentiated cells, or the number of cells expressing at least one marker expressed by an undifferentiated cell (such as TRA-1-60) within the mixed population may also be reduced.

In some embodiments the invention provides a method of reducing the number of extraneous phenotypic cells in a mixed population of cells comprising a) contacting the mixed population of cells with one or more ligands that specifically bind to the extraneous phenotypic cells; and b) separating the ligand bound extraneous phenotypic cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In other embodiments the invention provides a method of reducing the number of extraneous phenotypic cells in a mixed population of cells comprising a) contacting the mixed population of cells with one or more ligands that specifically bind to the extraneous phenotypic cells; and b) contacting the ligand bound extraneous phenotypic cells with a chemical agent that kills the ligand bound extraneous phenotype cell thereby reducing the number of extraneous phenotypic cells from a mixed population of cells, wherein the mixed population of cells comprises the in vitro differentiated progeny of pPS cells including the extraneous phenotypic cells.

In certain embodiments the invention provides a method of reducing the number of extraneous phenotypic cells in a mixed population of cells comprising a) contacting the mixed population of cells with one or more ligands that specifically bind to one or more markers expressed by an epithelial cell; and b) separating the ligand bound cells of a) from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In some embodiments the invention provides a method of reducing the number of extraneous phenotypic cells in a mixed population of cells comprising a) contacting the mixed population of cells with one or more ligands that specifically bind to one or more markers expressed by an epithelial cell; and b) contacting the ligand bound cells of a) with a chemical agent that kills the ligand bound cells of a) thereby reducing the number of extraneous phenotypic cells from a mixed population of cells, wherein the mixed population of cells comprises the in vitro differentiated progeny of pPS cells including the extraneous phenotypic cells.

In other embodiments the invention provides a method of reducing the number of extraneous phenotypic cells in a mixed population of cells comprising a) contacting the mixed population of cells with one or more ligands that specifically bind epithelial cells and contacting the mixed population of cells with one or more ligands that specifically bind to undifferentiated pPS cells; and b) separating the ligand bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In still other embodiments the invention provides a method of reducing the number of extraneous phenotypic cells in a mixed population of cells comprising a) contacting the mixed population of cells with one or more ligands that specifically bind epithelial cells and contacting the mixed population of cells with one or more ligands that specifically bind to undifferentiated pPS cells; and b) contacting the ligand bound cells of a) with a chemical agent that kills the ligand bound cells of a) thereby reducing the number of extraneous phenotypic cells from a mixed population of cells, wherein the mixed population of cells comprises the in vitro differentiated progeny of pPS cells including the extraneous phenotypic cells.

In yet other embodiments the invention provides a method of reducing the number of extraneous phenotypic cells in a mixed population of cells comprising a) contacting the mixed population of cells with one or more ligands that specifically bind to a molecule chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin); and b) separating the ligand bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In yet other embodiments the invention provides a method of reducing the number of extraneous phenotypic cells in a mixed population of cells comprising a) contacting the mixed population of cells with one or more ligands that specifically bind to a molecule chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin); and b) contacting the ligand bound cells of a) with a chemical agent that kills the ligand bound cells of a) thereby reducing the number of extraneous phenotypic cells from a mixed population of cells, wherein the mixed population of cells comprises the in vitro differentiated progeny of pPS cells including the extraneous phenotypic cells.

In further embodiments the invention provides a method of reducing the number of extraneous phenotypic cells in a mixed population of cells comprising a) contacting the mixed population of cells with one or more ligands chosen from cytokeratin, epithelial cell adhesion molecule (EpCAM) desmocollin 3; desmoglein 2; E-cadherin CD49f, EMA, E-cad, CD321 (Jam1), CD10 CD66, and CD105 (endoglin); b) contacting the mixed population of cells with one or more ligands that specifically bind to undifferentiated pPS cells; and c) contacting the ligand bound cells of a), b) or a) and b) with a with a chemical agent that kills the ligand bound cells, thereby reducing the number of extraneous phenotypic cells from a mixed population of cells, wherein the mixed population of cells comprises the in vitro differentiated progeny of pPS cells including the extraneous phenotypic cells.

In still further embodiments the invention provides a method of reducing the number of extraneous phenotypic cells in a mixed population of cells comprising a) contacting the mixed population of cells with one or more ligands chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin); b) contacting the mixed population of cells with a ligand that specifically bind to TRA-160; and c) separating the ligand bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In other embodiments the invention provides a method of reducing the number of extraneous phenotypic cells in a mixed population of cells comprising a) contacting the mixed population of cells with one or more ligands chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin); b) contacting the mixed population of cells with a ligand that specifically bind to TRA-160; and c) contacting the ligand bound cells of a), b) or a) and b) with a with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In certain other embodiments the invention provides a method of reducing the number of epithelial cells in a mixed population of cells comprising a) contacting the mixed population of cells with one or more ligands that specifically bind epithelial cells and b) separating the ligand bound epithelial cells from the rest of the mixed population of cells thereby reducing the number of epithelial cells from a mixed population of cells, wherein the mixed population of cells comprises the in vitro differentiated progeny of pPS cells including the extraneous phenotypic cells.

In certain other embodiments the invention provides a method of reducing the number of epithelial cells in a mixed population of cells comprising a) contacting the mixed population of cells with one or more ligands that specifically bind epithelial cells and b) contacting the cells of a) with a chemical agent that kills the ligand bound cells of a) thereby reducing the number of epithelial cells from a mixed population of cells, wherein the mixed population of cells comprises the in vitro differentiated progeny of pPS cells including the extraneous phenotypic cells.

In further embodiments the invention provides a method of reducing the number of epithelial cells in a mixed population of cells comprising a) contacting the mixed population of cells with one or more ligands that specifically bind one or more molecules chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin) and b) separating the ligand bound epithelial cells from the rest of the mixed population of cells thereby reducing the number of epithelial cells from a mixed population of cells, wherein the mixed population of cells comprises the in vitro differentiated progeny of pPS cells including the extraneous phenotypic cells.

In other embodiments the invention provides a method of reducing the number of epithelial cells in a mixed population of cells comprising a) contacting the mixed population of cells with one or more ligands that specifically bind one or more molecules chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin) and b) contacting the ligand bound epithelial cells with a chemical agent that kills the ligand bound cells thereby reducing the number of epithelial cells from a mixed population of cells, wherein the mixed population of cells comprises the in vitro differentiated progeny of pPS cells including the extraneous phenotypic cells.

In still other embodiments the invention provides a method of reducing the number of extraneous phenotypic cells in a mixed population of cells comprising a) contacting the mixed population of cells with one or more ligands that specifically bind to EpCAM and b) separating the EpCAM bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In other embodiments the invention provides a method of reducing the number of extraneous phenotypic cells in a mixed population of cells comprising a) contacting the mixed population of cells with one or more ligands that specifically bind to EpCAM and b) contacting the EpCAM bound cells with a chemical agent that kills the EpCAM bound cells thereby reducing the number of extraneous phenotypic cells from a mixed population of cells, wherein the mixed population of cells comprises the in vitro differentiated progeny of pPS cells including the extraneous phenotypic cells.

In further embodiments the invention provides a method of reducing the number of extraneous phenotypic cells in a mixed population of cells comprising a) contacting the mixed population of cells with one or more ligands that specifically bind to a cytokeratin molecule and b) separating the cytokeratin bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In other embodiments the invention provides a method of reducing the number of extraneous phenotypic cells in a mixed population of cells comprising a) contacting the mixed population of cells with one or more ligands that specifically bind to a cytokeratin molecule and b) contacting the cytokeratin bound cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In some embodiments the invention provides a method of reducing the number of extraneous phenotypic cells in a mixed population of cells comprising a) contacting the mixed population of cells with one or more ligands that specifically bind to a desmocollin 3 molecule and b) separating the desmocollin 3 bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In some embodiments the invention provides a method of reducing the number of extraneous phenotypic cells in a mixed population of cells comprising a) contacting the mixed population of cells with one or more ligands that specifically bind to a desmocollin 3 molecule and b) contacting the desmocollin 3 bound cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In further embodiments the invention provides a method of reducing the number of extraneous phenotypic cells in a mixed population of cells comprising a) contacting the mixed population of cells with one or more ligands that specifically bind to a desmoglein 2 molecule and b) separating the desmoglein 2 bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In still further embodiments the invention provides a method of reducing the number of extraneous phenotypic cells in a mixed population of cells comprising a) contacting the mixed population of cells with one or more ligands that specifically bind to a desmoglein 2 molecule and b) contacting the desmoglein 2 bound cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In still further embodiments the invention provides a method of reducing the number of extraneous phenotypic cells in a mixed population of cells comprising a) contacting the mixed population of cells with one or more ligands that specifically bind to a E-cadherin molecule and b) separating the E-cadherin bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In yet further embodiments the invention provides a method of reducing the number of extraneous phenotypic cells in a mixed population of cells comprising a) contacting the mixed population of cells with one or more ligands that specifically bind to a E-cadherin molecule and b) contacting the E-cadherin bound cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In still other embodiments the invention provides a method of reducing the number of extraneous phenotypic cells in a mixed population of cells comprising a) contacting the mixed population of cells with one or more ligands that specifically bind to a CD49f molecule and b) separating the CD49f bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In other embodiments the invention provides a method of reducing the number of extraneous phenotypic cells in a mixed population of cells comprising a) contacting the mixed population of cells with one or more ligands that specifically bind to a CD49f molecule and b) contacting the CD49f bound cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In still other embodiments the invention provides a method of reducing the number of extraneous phenotypic cells in a mixed population of cells comprising a) contacting the mixed population of cells with one or more ligands that specifically bind to a EMA molecule and b) separating the EMA bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In some embodiments the invention provides a method of reducing the number of extraneous phenotypic cells in a mixed population of cells comprising a) contacting the mixed population of cells with one or more ligands that specifically bind to a EMA molecule and b) contacting the EMA bound cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In further embodiments the invention provides a method of reducing the number of extraneous phenotypic cells in a mixed population of cells comprising a) contacting the mixed population of cells with one or more ligands that specifically bind to an E-cad molecule and b) separating the E-cad bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In yet further embodiments the invention provides a method of reducing the number of extraneous phenotypic cells in a mixed population of cells comprising a) contacting the mixed population of cells with one or more ligands that specifically bind to an E-cad molecule and b) contacting the E-cad bound cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In other embodiments the invention provides a method of reducing the number of extraneous phenotypic cells in a mixed population of cells comprising a) contacting the mixed population of cells with one or more ligands that specifically bind to a CD321 molecule and b) separating the CD321 bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In still other embodiments the invention provides a method of reducing the number of extraneous phenotypic cells in a mixed population of cells comprising a) contacting the mixed population of cells with one or more ligands that specifically bind to a CD321 molecule and b) contacting the CD321 bound cells with a chemical agent that kills the ligand bound cells f thereby reducing the number of extraneous phenotypic cells from a mixed population of cells, wherein the mixed population of cells comprises the in vitro differentiated progeny of pPS cells including the extraneous phenotypic cells.

In further embodiments the invention provides a method of reducing the number of extraneous phenotypic cells in a mixed population of cells comprising a) contacting the mixed population of cells with one or more ligands that specifically bind to a CD66 molecule and b) separating the CD66 bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In yet further embodiments the invention provides a method of reducing the number of extraneous phenotypic cells in a mixed population of cells comprising a) contacting the mixed population of cells with one or more ligands that specifically bind to a CD66 molecule and b) contacting the CD66 bound cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In further embodiments the invention provides a method of reducing the number of extraneous phenotypic cells in a mixed population of cells comprising a) contacting the mixed population of cells with one or more ligands that specifically bind to a CD10 molecule and b) separating the CD10 bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In other embodiments the invention provides a method of reducing the number of extraneous phenotypic cells in a mixed population of cells comprising a) contacting the mixed population of cells with one or more ligands that specifically bind to a CD10 molecule and b) contacting the CD10 bound cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In still further embodiments the invention provides a method of reducing the number of extraneous phenotypic cells in a mixed population of cells comprising a) contacting the mixed population of cells with one or more ligands that specifically bind to a CD105 molecule and b) separating the CD105 bound cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In other embodiments the invention provides a method of reducing the number of extraneous phenotypic cells in a mixed population of cells comprising a) contacting the mixed population of cells with one or more ligands that specifically bind to a CD105 molecule and b) contacting the CD105 bound cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In other embodiments the invention provides a method of reducing the number of cytokeratin expressing cells from a mixed population of cells comprising a) contacting the mixed population of cells with one or more ligands that specifically bind to EpCAM and b) separating the EpCAM bound cells from the rest of the mixed population of cells thereby reducing the number of cytokeratin cells from a mixed population of cells, wherein the mixed population of cells comprises the in vitro differentiated progeny of pPS cells including the cytokeratin expressing cells.

In certain other embodiments the invention provides a method of reducing the number of extraneous phenotypic cells in a mixed population of cells comprising a) contacting the mixed population of cells with one or more ligands that specifically bind to EpCAM and one or more ligands that specifically bind to a marker expressed on an undifferentiated cell; and b) separating the cells bound to the ligand for EpCAM and the cells bound to the ligand of a marker expressed on undifferentiated cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In other embodiments the invention provides a method of reducing the number of extraneous phenotypic cells in a mixed population of cells comprising a) contacting the mixed population of cells with one or more ligands that specifically bind to EpCAM and one or more ligands that specifically bind to a marker expressed on an undifferentiated cell; and b) contacting the cells bound to the ligand for EpCAM and/or the cells bound to the ligand of a marker expressed on undifferentiated cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In yet other embodiments the invention provides a method of reducing the number of extraneous phenotypic cells in a mixed population of cells comprising a) contacting the mixed population of cells with one or more ligands that specifically bind to EpCAM and one or more ligands that specifically bind to TRA-1-60; and b) separating the cells bound to the ligand for EpCAM and the cells bound to the ligand of TRA-1-60 from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In further embodiments the invention provides a method of reducing the number of extraneous phenotypic cells in a mixed population of cells comprising a) contacting the mixed population of cells with one or more ligands that specifically bind to EpCAM and one or more ligands that specifically bind to TRA-1-60; and b) contacting the cells bound to the ligand for EpCAM and/or the cells bound to the ligand of TRA-1-60 with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In certain other embodiments the invention provides a method of reducing the number of extraneous phenotypic cells in a mixed population of cells comprising a) contacting the mixed population of cells with one or more ligands that specifically bind to one or more molecules chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin) and one or more ligands that specifically bind to a marker expressed on an undifferentiated cell; and b) separating the cells bound to the one or more molecules chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin) and the cells bound to the ligand of a marker expressed on undifferentiated cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.

In further embodiments the invention provides a method of reducing the number of extraneous phenotypic cells in a mixed population of cells comprising a) contacting the mixed population of cells with one or more ligands that specifically bind to one or more molecules chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin) and one or more ligands that specifically bind to a marker expressed on an undifferentiated cell; and b) contacting the cells bound to the one or more ligands specifically to bound to one or more molecules chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin) and/or the cells bound to the ligand of a marker expressed on undifferentiated cells with a chemical agent that kills the ligand bound cells thereby reducing the number of extraneous phenotypic cells from a mixed population of cells, wherein the mixed population of cells comprises the in vitro differentiated progeny of pPS cells including the extraneous phenotypic cells.

In yet other embodiments the invention provides a method of reducing the number of epithelial cluster forming cells in a mixed population of cells comprising a) contacting the mixed population of cells with one or more ligands that specifically bind to one or more molecules chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin) and b) separating the ligand bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In further embodiments the invention provides a method of reducing the number of epithelial cluster forming cells in a mixed population of cells comprising a) contacting the mixed population of cells with one or more ligands that specifically bind to one or more molecules chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin) and b) contacting the ligand bound cells of a) with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In yet other embodiments the invention provides a method of reducing the number of epithelial cluster forming cells in a mixed population of cells comprising a) contacting the mixed population of cells with one or more ligands that specifically bind to EpCAM and b) separating the EpCAM bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In still other embodiments the invention provides a method of reducing the number of epithelial cluster forming cells in a mixed population of cells comprising a) contacting the mixed population of cells with one or more ligands that specifically bind to EpCAM and b) contacting the EpCAM bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In still other embodiments the invention provides a method of reducing the number of epithelial cluster forming cells in a mixed population of cells comprising a) contacting the mixed population of cells with one or more ligands that specifically bind to a cytokeratin and b) separating the cytokeratin bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In further embodiments the invention provides a method of reducing the number of epithelial cluster forming cells in a mixed population of cells comprising a) contacting the mixed population of cells with one or more ligands that specifically bind to a cytokeratin and b) contacting the cytokeratin bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In yet further embodiments the invention provides a method of reducing the number of epithelial cluster forming cells in a mixed population of cells comprising a) contacting the mixed population of cells with one or more ligands that specifically bind to desmocollin 3 and b) separating the desmocollin 3 bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In other embodiments the invention provides a method of reducing the number of epithelial cluster forming cells in a mixed population of cells comprising a) contacting the mixed population of cells with one or more ligands that specifically bind to desmocollin 3 and b) contacting the desmocollin 3 bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In still other embodiments the invention provides a method of reducing the number of epithelial cluster forming cells in a mixed population of cells comprising a) contacting the mixed population of cells with one or more ligands that specifically bind to desmoglein 2 and b) separating the desmoglein 2 bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In other embodiments the invention provides a method of reducing the number of epithelial cluster forming cells in a mixed population of cells comprising a) contacting the mixed population of cells with one or more ligands that specifically bind to desmoglein 2 and b) contacting the desmoglein 2 bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In still further embodiments the invention provides a method of reducing the number of epithelial cluster forming cells in a mixed population of cells comprising a) contacting the mixed population of cells with one or more ligands that specifically bind to E-cadherin and b) separating the E-cadherin bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In further embodiments the invention provides a method of reducing the number of epithelial cluster forming cells in a mixed population of cells comprising a) contacting the mixed population of cells with one or more ligands that specifically bind to E-cadherin and b) contacting the E-cadherin bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In still other embodiments the invention provides a method of reducing the number of epithelial cluster forming cells in a mixed population of cells comprising a) contacting the mixed population of cells with one or more ligands that specifically bind to CD49f and b) separating the CD49f bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In other embodiments the invention provides a method of reducing the number of epithelial cluster forming cells in a mixed population of cells comprising a) contacting the mixed population of cells with one or more ligands that specifically bind to CD49f and b) contacting the CD49f bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In still other embodiments the invention provides a method of reducing the number of epithelial cluster forming cells in a mixed population of cells comprising a) contacting the mixed population of cells with one or more ligands that specifically bind to EMA and b) separating the EMA bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In other embodiments the invention provides a method of reducing the number of epithelial cluster forming cells in a mixed population of cells comprising a) contacting the mixed population of cells with one or more ligands that specifically bind to EMA and b) contacting the EMA bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In further embodiments the invention provides a method of reducing the number of epithelial cluster forming cells in a mixed population of cells comprising a) contacting the mixed population of cells with one or more ligands that specifically bind to a E-cad and b) separating the E-cad bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In still further embodiments the invention provides a method of reducing the number of epithelial cluster forming cells in a mixed population of cells comprising a) contacting the mixed population of cells with one or more ligands that specifically bind to a E-cad and b) contacting the E-cad bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In yet other embodiments the invention provides a method of reducing the number of epithelial cluster forming cells in a mixed population of cells comprising a) contacting the mixed population of cells with one or more ligands that specifically bind to CD321 and b) separating the CD321 bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In yet other embodiments the invention provides a method of reducing the number of epithelial cluster forming cells in a mixed population of cells comprising a) contacting the mixed population of cells with one or more ligands that specifically bind to CD321 and b) contacting the CD321 bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In still other embodiments the invention provides a method of reducing the number of epithelial cluster forming cells in a mixed population of cells comprising a) contacting the mixed population of cells with one or more ligands that specifically bind to CD66 and b) separating the CD66 bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In other embodiments the invention provides a method of reducing the number of epithelial cluster forming cells in a mixed population of cells comprising a) contacting the mixed population of cells with one or more ligands that specifically bind to CD66 and b) contacting the CD66 bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In still other embodiments the invention provides a method of reducing the number of epithelial cluster forming cells in a mixed population of cells comprising a) contacting the mixed population of cells with one or more ligands that specifically bind to CD10 and b) separating the CD10 bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In other embodiments the invention provides a method of reducing the number of epithelial cluster forming cells in a mixed population of cells comprising a) contacting the mixed population of cells with one or more ligands that specifically bind to CD10 and b) contacting the CD10 bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells In still other embodiments the invention provides a method of reducing the number of epithelial cluster forming cells in a mixed population of cells comprising a) contacting the mixed population of cells with one or more ligands that specifically bind to CD105 and b) separating the CD105 bound cells from the rest of the mixed population of cells thereby reducing the number of epithelial cluster forming cells from a mixed population of cells, wherein the mixed population of cells comprises the in vitro differentiated progeny of pPS cells including the epithelial cluster forming cells.

In other embodiments the invention provides a method of reducing the number of epithelial cluster forming cells in a mixed population of cells comprising a) contacting the mixed population of cells with one or more ligands that specifically bind to CD105 and b) contacting the CD105 bound cells with a chemical agent that kills the ligand bound cells thereby reducing the number of epithelial cluster forming cells from a mixed population of cells, wherein the mixed population of cells comprises the in vitro differentiated progeny of pPS cells including the epithelial cluster forming cells.

In further embodiments the invention provides a method of reducing the number of undifferentiated cells in a mixed population of cells comprising a) contacting the mixed population of cells with one or more ligands that specifically bind to the undifferentiated cells; and b) removing the ligand bound undifferentiated cells from the rest of the mixed population of cells thereby reducing the number of undifferentiated cells from a mixed population of cells wherein the mixed population of cells comprises the in vitro differentiated progeny of pPS cells. In some embodiments the ligand may include an antibody, such as an IgG that binds specifically to TRA-1-60.

In yet other embodiments the invention provides a method of reducing the number of cells expressing one or more molecules expressed by undifferentiated cells in a mixed population of cells comprising a) contacting the mixed population of cells with one or more ligands that specifically bind to an epithelial cell; and b) removing the ligand bound cells of a) from the rest of the mixed population of cells thereby reducing the number of undifferentiated cells from a mixed population of cells, wherein the mixed population of cells comprises the in vitro differentiated progeny of pPS cells.

In further embodiments the invention provides a method of reducing the number of cells expressing one or more molecules expressed by undifferentiated cells in a mixed population of cells comprising a) contacting the mixed population of cells with one or more ligands that specifically bind to EpCAM and b) removing the ligand bound EpCAM cells from the rest of the mixed population of cells thereby reducing the number of undifferentiated cells from a mixed population of cells, wherein the mixed population of cells comprises the in vitro differentiated progeny of pPS cells.

In still other embodiments the invention provides a method of reducing the number of cells expressing one or more molecules expressed by undifferentiated cells in a mixed population of cells comprising a) contacting the mixed population of cells with one or more ligands that specifically bind to EpCAM and one or more ligands that specifically bind to TRA-1-60 and b) removing the ligand bound cells from the rest of the mixed population of cells thereby reducing the number of undifferentiated cells from a mixed population of cells, wherein the mixed population of cells comprises the in vitro differentiated progeny of pPS cells.

In yet other embodiments the invention provides a method of reducing the number of cells expressing one or more molecules expressed by undifferentiated cells in a mixed population of cells comprising a) contacting the mixed population of cells with one or more ligands that specifically bind to a cytokeratin and b) removing the ligand bound cytokeratin cells from the rest of the mixed population of cells thereby reducing the number of undifferentiated cells from a mixed population of cells, wherein the mixed population of cells comprises the in vitro differentiated progeny of pPS cells.

In further embodiments the invention provides a method of reducing the number of cells expressing one or more molecules expressed by undifferentiated cells in a mixed population of cells comprising a) contacting the mixed population of cells with one or more ligands that specifically bind to a cytokeratin and one or more ligands that specifically bind to TRA-1-60 and b) removing the ligand bound cells from the rest of the mixed population of cells thereby reducing the number of undifferentiated cells from a mixed population of cells, wherein the mixed population of cells comprises the in vitro differentiated progeny of pPS cells.

In yet other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing a molecule found on an epithelial cell.

In still other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing a molecule found on an epithelial cell and at least one cell expressing a molecule found on an undifferentiated stem cell.

In other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing one or more of the molecules chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin).

In yet further embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing EpCAM.

In still other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing a cytokeratin.

In still other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing desmocollin 3.

In still other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing desmoglein 2.

In other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing E-cadherin.

In still other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing CD49f.

In further embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing EMA.

In still other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing E-cad.

In yet other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing CD321.

In still other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing CD166.

In still other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing CD105.

In further embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing one or more molecules chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin) and at least one cell expressing a marker found on an undifferentiated primate pluripotent cell In other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing EpCAM and at least one cell expressing a marker found on an undifferentiated primate pluripotent cell.

In still further embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing a cytokeratin and at least one cell expressing a marker found on an undifferentiated primate pluripotent stem cell.

In other embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing EpCAM and at least one cell expressing TRA-1-60.

In yet further embodiments the invention provides a mixed population of cells that is enriched for a targeted phenotype, wherein the mixed population of cells comprises the in vitro differentiated progeny of pPS cells and wherein the mixed population of cells has been depleted of at least one cell expressing a cytokeratin and at least one cell expressing TRA-1-60.

In still other embodiments the invention provides a method of transplanting into a subject a population of cells comprising cells having a targeted phenotype comprising a) obtaining a population of cells comprising the targeted phenotype, wherein the population of cells has been depleted of a least one cell having an extraneous phenotype; and b) administering the population of cells from a) to the subject.

In yet other embodiments the invention provides a method of treating a subject in need of cellular therapy comprising a) obtaining a population of cells comprising cells having a targeted phenotype, wherein the population of cells has been depleted of a least one cell having an extraneous phenotype and b) administering the population of cells from a) to the subject.

In further embodiments the invention provides the use of a population of cells for treating a subject in need of cellular therapy comprising cells having a targeted phenotype, wherein the population of cells has been depleted of a least one cell having an extraneous phenotype.

In still other embodiments the invention provides a method of transplanting into a subject a population of cells comprising cells having a targeted phenotype comprising a) obtaining a population of cells comprising cells having a targeted phenotype, wherein the population of cells has been depleted of a least one cell expressing an epithelial cell marker, and b) administering the population of cells from a) to the subject.

In yet other embodiments the invention provides a method of treating a subject in need of cellular therapy comprising a) obtaining a population of cells comprising cells having a targeted phenotype, wherein the population of cells has been depleted of a least one cell expressing an epithelial cell marker; and b) administering the population of cells from a) to the subject.

In further embodiments the invention provides the use of a population of cells for treating a subject in need of cellular therapy comprising cells having a targeted phenotype, wherein the population of cells has been depleted of a least one cell expressing an epithelial cell marker.

In other embodiments the invention provides a kit for depleting cells having an extraneous phenotype from a mixed population of cells comprising a) a ligand for one or more molecules expressed on an epithelial cell; b) a ligand for one or more molecules expressed on an undifferentiated cell; and c) one or more containers, wherein the mixed population of cells comprises the in vitro differentiated progeny of pPS cells.

In other embodiments the invention provides a kit for depleting cells having an extraneous phenotype from a mixed population of cells comprising a) a ligand for one or more molecules chosen from cytokeratin, epithelial cell adhesion molecule (EpCAM) desmocollin 3; desmoglein 2; E-cadherin CD49f, epithelial membrane antigen (EMA), E-cad, CD321 (Jam 1), CD10, CD66, and CD105 (endoglin); b) a ligand for one or more molecules expressed on an undifferentiated cell; and c) one or more containers, wherein the mixed population of cells comprises the in vitro differentiated progeny of pPS cells.

In further embodiments the invention provides a kit for depleting cells having an extraneous phenotype from a mixed population of cells comprising a ligand for EpCAM, a ligand for TRA-1-60 and one or more containers, wherein the mixed population of cells comprises the in vitro differentiated progeny of pPS cells.

In further embodiments the invention provides a kit for depleting cells having an extraneous phenotype from a mixed population of cells comprising a ligand for a cytokeratin, a ligand for TRA-1-60 and one or more containers, wherein the mixed population of cells comprises the in vitro differentiated progeny of pPS cells.

In other embodiments the invention provides a kit for depleting cells having an extraneous phenotype from a mixed population of cells comprising a) a ligand for one or more molecules chosen from cytokeratin, epithelial cell adhesion molecule (EpCAM) desmocollin 3; desmoglein 2; E-cadherin CD49f, EMA, E-cad, CD321 (Jam1), CD10, CD66, and CD105 (endoglin); and b) one or more containers, wherein the mixed population of cells comprises the in vitro differentiated progeny of pPS cells.

In still other embodiments the invention provides an antibody that binds specifically to TRA-1-60 wherein the antibody has an IgG isotype.

DESCRIPTION OF THE FIGURES

FIG. 10A, 10B, and FIG. 10C show data acquired by flow cytometry using either an EpCAM specific antibody followed by labeled secondary antibody (A647) or an isotype control (mIgG1) followed by the same secondary antibody. FIG. 10A shows data acquired by flow cytometry of cells that do not express EpCAM (HEK 293) spiked with EpCAM+ cells (SW480) to create a mixed population (10% SW480; 90% 293). FIG. 10B shows the flow cytometry data of the mixed population subjected to separation using magnetic beads conjugated to an EpCAM-specific antibody. FIG. 10C lists both the input and cell counts as well as an efficiency percentage.

FIG. 11 shows data acquired by flow cytometry. A single lot of oligodendroglial progenitor cells differentiated in vitro from hES cells was depleted of EpCAM positive cells using an EpCAM-specific antibody conjugated to a magnetic bead. The resulting cell fractions were labeled for TRA-1-60 and pan-cytokeratin using antibodies specific for each. The TRA-1-60 labeled cells were stained with a secondary antibody as well.

DEFINITIONS

Figure 1:
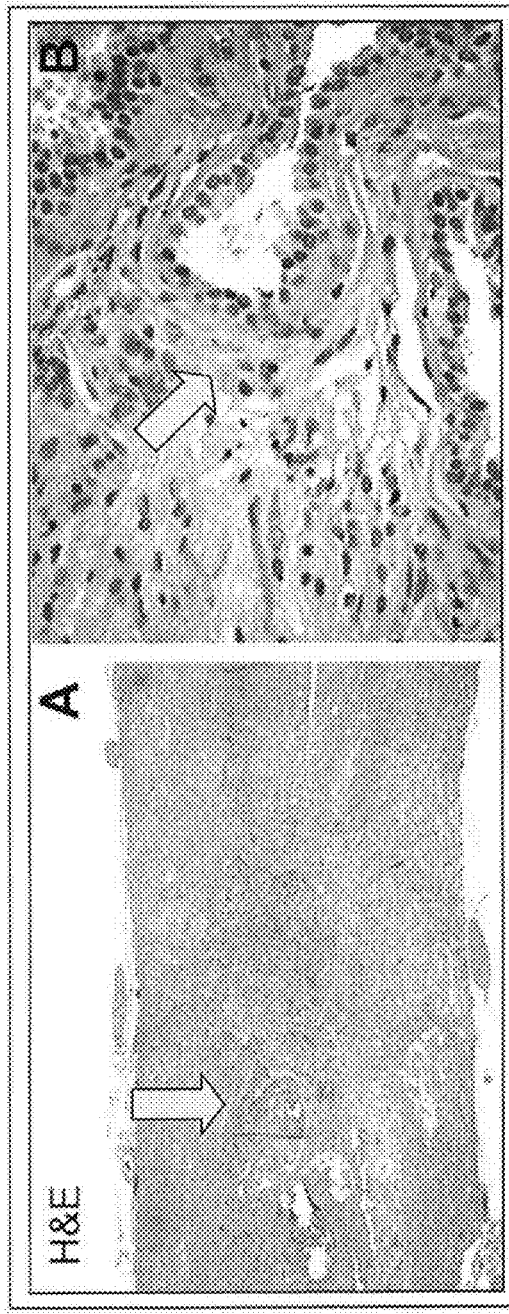
FIG. 1 is a photomicrograph showing the clustered epithelial structures, present in a small percentage of rats administered oligodendroglial progenitor cells differentiated in vitro from hES cells, have an epithelial-like morphology.

"About," as used herein to refer to an amount or a value means + or −5% of stated amount or value.

"Cardiomyocytes," as used herein includes mature cardiomyocytes (a cell that possesses the functional capability of a cardiomyocyte isolated from either a juvenile or adult primate) and/or cardiomyocyte precursors (cells which express one or markers expressed on, in, or by cardiomyocytes and/or have one or more morphological attributes associated with cardiomyocytes and which may differentiate into mature cardiomyocyte either in vitro or when implanted into a subject).

"Cell culture," as used herein, refers to a plurality of cells grown in vitro over time. The cell culture may originate from a plurality of pPS cells or from a single pPS cell and may include all of the progeny of the originating cell or cells, regardless of 1) the number of passages or divisions the cell culture undergoes over the lifetime of the culture; and 2) any changes in phenotype to one or more cells within the culture over the lifetime of the culture. Thus, as used herein, a cell culture begins with the initial seeding of one or more suitable vessels with at least one pPS cell and ends when the last surviving progeny of the original founder(s) is harvested or dies. Seeding of one or more additional culture vessels with progeny of the original founder cells is also considered to be a part of the original cell culture.

"Chondrocyte," as used herein, includes mature chondrocytes (a cell that possesses the functional capability of a chondrocyte isolated from either a juvenile or adult primate) and/or chondrocyte precursors (cells which express one or markers expressed on, in, or by chondrocytes and/or have one or more morphological attributes associated with chondrocytes and which may differentiate into mature chondrocytes either in vitro or when implanted into a subject).

"Clustered epithelial structures" as used herein, refers to a structure that may form when extraneous phenotypic cells of epithelial lineage found in a mixed population of cells comprising the in vitro differentiated progeny of pPS cells are implanted into a subject. These structures have the morphology of epithelial cells and express at least one molecular marker expressed in epithelial cells as described infra. In some instances the structures may have the form of a sac or vesicle.

"Cytokeratin," as used herein, refers to intermediate filament keratins found in the intracytoplasmic cytoskeleton of epithelial tissue. There are two types of cytokeratins: acidic types I cytokeratins and basic or neutral type II cytokeratins. Cytokeratins are usually found in pairs comprising a type I cytokeratin and a type II cytokeratin. The type II cytokeratins, which are the basic or neutral cytokeratins, comprise subtypes CK1, CK2, CK3, CK4, CK5, CK6a, CK6b, CK6c, CK7 and CK80. The type I cytokeratins, which are the acidic cytokeratins, comprise subtypes CK9, CK10, CK12, CK13, CK14, CK15, CK16, CK17, CK18, CK19, CK20, CK23 and CK24. All cytokeratin proteins contain a central α-helix-rich domain (with a 50-90% sequence identity among cytokeratins of the same type and around 30% between cytokeratins of different types) with non-α-helical N- and C-terminal domains.

"Depleted," as used herein, refers to an act by which an extraneous phenotype contained within a mixed population of cells has been decreased in number relative to other phenotypic cell types within the population as a result of an act initiated by the human hand. Included are methods where the extraneous phenotype is physically segregated from the other cells in the population, as for example by immuno-precipitating the extraneous phenotypic cells. Also included are methods where the extraneous phenotypic cells are removed chemically from the rest of the population, e.g., where the extraneous phenotypic cell is specifically targeted with a chemical agent such as a toxin, complement and the like. Thus cell populations depleted of one or more cells having an extraneous phenotype are considered to be depleted. Typically the depletion is measured by comparing the number of cells bearing the extraneous phenotype before and after the act initiated by the human hand whereby any decrease in the relative number of the cell population bearing the extraneous phenotype as a result of the act initiated by the human hand is considered depletion. Depletion of an extraneous phenotype from a mixed population of cells may result in the enrichment of a target cell population within the mixed population of cells.

"Desmocollin 3," as used herein, refers to an epithelial cell marker that is a calcium-dependent glycoprotein that is a member of the desmocollin subfamily of the cadherin superfamily. These desmosomal family members, along with the desmogleins, are found primarily in epithelial cells where they constitute the adhesive proteins of the desmosome cell-cell junction and are required for cell adhesion and desmosome formation. The desmosomal family members are arranged in two clusters on chromosome 18, occupying less than 650 kb combined. Alternative splicing results in two transcript variants encoding distinct isoforms.

"Desmoglein 2," as used herein, refers to an epithelial cell marker. Desmoglein 2 is a calcium-binding transmembrane glycoprotein component of desmosomes in vertebrate epithelial cells. Desmosomes are cell-cell junctions between epithelial, myocardial, and certain other cell types. Currently, three desmoglein subfamily members have been identified and all are members of the cadherin cell adhesion molecule superfamily. These desmoglein gene family members are located in a cluster on chromosome 18. This second family member is expressed in colon, colon carcinoma, and other simple and stratified epithelial-derived cells.

"E-cadherin" (CD324), as used herein, refers to an epithelial cell marker expressed on the cell surface. It is a calcium dependent cell-cell adhesion glycoprotein comprised of five extracellular cadherin repeats, a transmembrane region and a highly conserved cytoplasmic tail. Mutations in this gene are correlated with gastric, breast, colorectal, thyroid and ovarian cancer. Loss of function is thought to contribute to progression in cancer by increasing proliferation, invasion, and/or metastasis. The ectodomain of this protein mediates bacterial adhesion to mammalian cells and the cytoplasmic domain is required for internalization.

"Enriched," as use herein, refers to an act initiated by the human hand by which a target phenotype contained within a mixed population of cells has increased in number relative to other phenotypic cell types within the population. Typically the enrichment is measured by comparing the number of target phenotypic cells before and after the act initiated by the human hand whereby any increase in the relative number of the targeted cell population as a result of the act initiated by the human hand is considered enrichment.

"Embryold bodies," as used herein, refers to heterogeneous clusters comprising undifferentiated, differentiated and partly differentiated cells that appear when primate pluripotent stem cells are allowed to differentiate in a non-specific fashion in suspension cultures or aggregates.

As used herein, "embryonic stem cell" (ES) refers to pluripotent stem cells that are 1) derived from a blastocyst before substantial differentiation of the cells into the three germ layers or 2) alternatively obtained from an established cell line. Except where explicitly required otherwise, the term includes primary tissue and established lines that bear phenotypic characteristics of ES cells, and progeny of such lines that have the pluripotent phenotype. The ES cells may be human ES cells (hES). Prototype "human Embryonic Stem cells" (hES cells) are described by Thomson et al. (*Science* 282:1145, 1998; U.S. Pat. No. 6,200,806) and may be obtained from any one of a number of established stem cell banks such as the UK Stem Cell Bank (Hertfordshire, England) and the National Stem Cell Bank (Madison, Wis.).

"EpCAM," as used herein, refers to Epithelial Cell Adhesion Molecule an epithelial cell marker. It is a pan-epithelial differentiation antigen that is expressed on epithelial cells and almost all carcinomas.

"Epithelial cells," as used herein, refers to cells having a morphology chosen from a) squamous (thin flat); b) cuboidal (cube like); c) columnar (tall) d) pseudostratified (all cells reach the basement membrane, and some extend all the way to the surface, while others do not; e) transitional (e.g. as found in the urinary bladder) where cells may appear squamous under some conditions and rounded under other conditions; and express at least one marker associated with epithelial cells. Exemplary epithelial markers include EpCAM; cytokeratin; desmocollin 3; desmoglein 2; E-cadherin CD49f, EMA, E-cad, CD321 (Jam1), CD10, CD66, and CD105 (endoglin).

"Extraneous phenotype," as used herein, refers to one or more cell types contained within a mixed population of cells that are undesirable. Thus in a mixed population of cells comprising a target phenotypic cell population, any cell having a phenotype that differs from the target population may be considered extraneous. Extraneous phenotypic cells may be targeted for depletion. An example of an extraneous phenotypic cell is a cell that has the potential to form a clustered epithelial structure when administered to a subject and that expresses one or more markers expressed by an epithelial cell.

"Hematopoietic cells," as used herein, includes mature hematopoietic cells (a cell that possesses the functional capability of a hematopoietic cell isolated from either a juvenile or adult primate) such as dendritic cells, macrophages, B lymphocytes, T lymphocytes including both CD8+ and CD4+ lymphocytes, neutrophils, basophils, cosinophils, natural killer (NK) cells, platelets, erythrocytes and mast cells and/or hematopoietic precursors (cells which express one or markers expressed on, in, or by a hematopoietic cell and/or have one or more morphological attributes associated with a hematopoietic cell and which may differentiate into mature hematopoietic cells either in vitro or when implanted into a subject).

"Hepatocytes," as used herein, includes mature hepatocytes (a cell that possesses the functional capability of a hepatocyte isolated from either a juvenile or adult primate) and/or hepatocyte precursors (cells which express one or markers expressed on, in, or by hepatocytes and/or have one or more morphological attributes associated with hepatocytes and which may differentiate into mature hepatocytes either in vitro or when implanted into a subject).

"Islet cells," or "pancreatic islet cells," as used herein, includes mature islet cells (a cell that possesses the functional capability of an islet cell isolated from either a juvenile or adult primate) and/or islet cell precursors (cells which express one or more markers expressed on, in, or by islet cells and/or have one or more morphological attributes associated with islet cells and which may differentiate into mature islet cells either in vitro or in vivo, i.e., when implanted into a subject).

In vitro differentiated progeny, as used herein, refers to cells that have been differentiated from pPS cells in vitro by the addition of one or more growth factors, cytokines, morphogens, or the like, that are added by the human hand to a culture of pPS cells or to a culture of pPS cells that have already begun to differentiate down one or more specific pathways. Additional suitable agents that may be useful in differentiating pPS include micro RNA molecules, siRNA molecules, and small molecules such as IDE1, IDE2, -(-) Indolactan and Stauplimide. (see, Borowick et al. (2009) *Cell Stem Cell* 4:348; Chen et al. (2009) *Nature Chem Biol* 4:258; Zhu (2009) *Cell Stem Cell* 4:416). Excluded from the definition are the random or spontaneous differentiation events obtained by merely forming an embryoid body or by merely allowing a culture of pPS cells to overgrow the vessel containing them without the addition of one or more growth factors, cytokines, morphogen or the like (beyond what may be found in commercially available cell culture media or commercially available serum products or serum replacement products). However, cells that have been differentiated from embryoid bodies are included in the definition provided that one or more growth factors, cytokines, morphogens or the like have been added to the culture to facilitate the differentiation down a particular pathway to obtain a target phenotype.

"Ligand," as used herein, refers to a first molecule that specifically interacts with a second molecule to form a chemical bond. Typically, the bond will be a non-covalent bond such as an ionic interaction, a hydrogen bond or an interaction mediated by Van der Waals forces. Examples of ligand pairs (i.e. the first and second molecule referred to above) include an epitope and an antibody that binds specifically to that epitope and a substrate that specifically binds an enzyme. The dissociation constant ($K_d$) between the two molecules is one measure of the affinity between a ligand and its specific binding partner. Specific interactions are typically characterized by relatively small $K_d$. An example of a ligand pair that bind each other with very high affinity (very small $K_d$) is biotin/avidin. In contrast, non-specific binding between two molecules may involve the formation of chemical bonds based on charge and hydrophobicity, however, unlike specific binding, the interactions are not based on the exact structure of the two molecules.

"Mixed population of cells," as used herein, refers to an in vitro culture of cells comprised of more than one phenotype.

"Oligodendrocytes," as used herein, includes mature oligodendrocytes (a cell that possesses the functional capability of an oligodendrocyte isolated from either a juvenile or adult primate) and/or oligodendrocyte precursors (cells which express one or markers expressed on, in, or by oligodendrocytes and/or have one or more morphological attributes associated with oligodendrocytes and which may differentiate into mature oligodendrocytes either in vitro or when implanted into a subject).

"Osteoblast," as used herein, includes mature osteoblasts (a cell that possesses the functional capability of an osteoblast isolated from either a juvenile or adult primate) and/or osteoblast precursors (cells which express one or markers expressed on, in, or by osteoblast and/or have one or more morphological attributes associated with oligodendrocytes and which may differentiate into mature oligodendrocytes either in vitro or when implanted into a subject).

"Pan-cytokeratin," as used herein, refers to an antibody or a mixture of antibodies that bind to epitopes expressed on or in at least a plurality of cytokeratin family members.

As used herein, "primate pluripotent stem cells" (pPS) refers to cells that may be derived from any source and that are capable, under appropriate conditions, of producing primate progeny of different cell types that are derivatives of all of the 3 germinal layers (endoderm, mesoderm, and ectoderm). pPS cells may have the ability to form a teratoma in 8-12 week old SCID mice and/or the ability to form identifiable cells of all three germ layers in tissue culture. Included in the definition of primate pluripotent stem cells are embryonic cells of various types including human embryonic stem (hES) cells, (see, e.g., Thomson et al. (1998) *Science* 282:1145) and human embryonic germ (hEG) cells (see, e.g., Shamblott et al., (1998) *Proc. Natl. Acad. Sci. USA* 95:13726,); embryonic stem cells from other primates, such as Rhesus stem cells (see, e.g., Thomson et al., (1995) *Proc. Natl. Acad. Sci. USA* 92:7844), marmoset stem cells (see, e.g., (1996) Thomson et al., *Biol. Reprod.* 55:254,), stem cells created by nuclear transfer technology (U.S. Patent Application Publication No. 2002/0046410), as well as induced pluripotent stem cells (see, e.g. Yu et al., (2007) *Science* 318:5858); Takahashi et al., (2007) *Cell* 131(5):861). The pPS cells may be established as cell lines, thus providing a continual source of pPS cells. It is contemplated that any of the embodiments of the invention described herein may be practiced by substituting one or more of the following sub-groupings of pPS cells for pPS cells: human embryonic stem cells, human embryonic germ cells, rhesus stem cells, marmoset stem cells, nuclear transfer stem cells and/or induced pluripotent stem cells.

"Target phenotype" or "targeted phenotype," as used herein, refers to a desirable cell type differentiated in vitro from a pPS cell.

As used herein, "undifferentiated primate pluripotent stem cells" refers to a cell culture where a substantial proportion of primate pluripotent stem cells and their derivatives in the population display morphological characteristics of undifferentiated cells and maintain the capacity to give rise to at least one cell type from each of the three germ layers: endoderm, mesoderm and ectoderm. It is understood that colonies of undifferentiated cells within the population may be surrounded by neighboring cells that are partly differentiated.

Treat, treatment, treating, as used herein, means any of the following: the reduction in severity of a disease or condition; the reduction in the duration of a disease course; the amelioration of one or more symptoms associated with a disease or condition; the provision of beneficial effects to a subject with a disease or condition, without necessarily curing the disease or condition, the prophylaxis of one or more symptoms associated with a disease or condition.

DETAILED DESCRIPTION OF THE INVENTION

The invention relates, at least in part, to the discovery that extraneous phenotypes may sometimes exist in cell cultures comprising the in vitro differentiated progeny of pPS cells. Typically these extraneous phenotypes are rare and present at low levels. The extraneous phenotypes may manifest themselves, e.g. by multiplying in vivo when the in vitro differentiated progeny of pPS cells are administered to a subject. One example of an extraneous phenotypic cell is a cell that has the capacity to develop into a clustered epithelial structure when implanted into a subject. Cells which have the capacity to develop into a clustered epithelial structure when implanted into a subject may typically express one or more markers expressed by an epithelial cell.

It has been discovered that certain extraneous phenotypic cells may be identified by the presence of epithelial cell markers such as EpCAM, desmocollin 3; desmoglein 2; E-cadherin CD49f, EMA, E-cad, CD321 (Jam1), CD10, CD66, CD105 (endoglin), cytokeratin and the like. Epithelial markers expressed on the cell surface of the extraneous phenotypic cells provide suitable markers both for identifying the presence of extraneous phenotypic cells and for targeting these cells for depletion. EpCAM is an example of such a marker. EpCam may be targeted for depletion either alone or in combination with one of more markers described infra. Thus EpCAM may be targeted for depletion along with a marker found on undifferentiated cells such as TRA-160. Other examples include one or more of the following markers: desmocollin 3; desmoglein 2; E-cadherin CD49f, EMA, E-cad, CD321 (Jam1), CD10, CD66, and CD105 (endoglin). Accordingly, the markers described infra may be used in targeting these cells for removal/depletion from a mixed population of cells that includes cells having an extraneous phenotype or that includes cells that may develop into cells having an extraneous phenotype, e.g., when implanted into a subject.

Surprisingly, it was also discovered that certain sub-populations of cells that express these epithelial markers also express markers found on undifferentiated pPS cells such as TRA-1-60. Thus targeting cells expressing epithelial cell markers with a suitable ligand may not only decrease the number of extraneous phenotypic cells in the population; it may also facilitate minimizing the number of cells expressing markers associated with undifferentiated pPS cells in the cell culture, which may include pluripotent stem cells.

Methods of Reducing Extraneous Phenotypic Cells from a Mixed Population of Cells In certain embodiments the invention provides a method of reducing the number of extraneous phenotypic cells from a mixed population of cells comprising contacting the mixed population of cells with one or more ligands that bind to the cells having the extraneous phenotype and then separating the extraneous phenotypic cells from the population. The mixed population of cells may comprise the in vitro differentiated progeny of pPS cells.

The mixed cell population may be contacted with ligand in a suitable buffer. Suitable buffers may include phosphate buffered saline (PBS) or any commercially available cell culture media that facilitates survival of the mixed population of cells. Typically the buffer will be an isotonic buffer and have a pH ranging from about 6.8 to about 7.7, from about 6.9 to about 7.6; from about 7.0 to about 7.5. In some embodiments the pH of the buffer will be physiological pH.

The method is adaptable over a wide range of sample volumes ranging from sample sizes obtainable from a single well of a microwell plate to a sample obtained from a scale-up bioreactor. A suitable volume for contacting the mixed cell population can range from about 50 µL to about 10,000 liters. In some embodiments a suitable volume for contacting the mixture of cells is about 100 µL, about 200 µL, about 500 µL, about 1 mL, about 10 mL, about 50 mL, about 100 mL, about 1 liter, about 10 liters, about 50 liters, about 100 liters, about 1000 liters, about 2000 liters, about 5000 liters, about 8,000 liters, about 10,000 liters or more.

Any suitable ratio of ligands to cell number comprising the mixed cell population may be used. For example a suitable ratio of ligand to cell number may be about 1:1; about 10:1; about 100:1; about 1000:1; about 10,000:1; about $10^5$:1; about $10^6$:1; about $10^7$:1; about $10^8$:1; about $10^9$:1; about $10^{10}$:1.

In some embodiments the ligand may be linked to a solid support such as a bead. A plurality of ligand linked beads may be used to reduce the number of extraneous phenotypic cells present in a mixed population of cells. For example, a suitable number of beads may range from about 1 bead per cell; about 5 beads per cell; about 10 beads per cell; about 15 beads per cell; about 20 beads per cell; about 25 beads per cell; about 30 beads per cell; about beads per cell; about 40 beads per cell; about 45 beads per cell; about 50 beads per cell; about 60 beads per cell; about 70 beads per cell; about 80 beads per cell; about 90 beads per cell; about 100 beads per cell. To each bead in turn may be linked to at least 10 ligands; at least 100 ligands; at least 1000 ligands; at least 10,000 ligands; at least $10^5$ ligands; at least $10^6$ ligands; at least $10^7$ ligands; at least $10^8$ ligands; at least $10^9$ ligands; at least $10^{10}$ ligands; at least $10^{20}$ ligands; at least $10^{30}$ ligands at least $10^{40}$ ligands at least $10^{50}$ ligands.

Typically the method of the invention comprises a step of co-incubating the ligand and the mixed cell population to facilitate binding of the ligand to an extraneous phenotypic cell expressing a binding partner of the ligand. The ligand and mixed cell population may be incubated at a temperature ranging from about 3° C. to about 40° C. In some embodiments the ligand and the mixed cell population may be incubated at about 4° C.; about 20° C.; about 37° C. A suitable length of time for incubating the ligand and the mixed population of cells may range from about 1 minute to about 60 minutes; about 5 minutes to about 50 minutes; about 10 minutes to about 40 minutes. In some embodiments the ligand and mixed cell population may incubated for about 10 minutes; about 15 minutes; about 20 minutes; about 25 minutes; about minutes; about 60 minutes. After contacting the mixed cell population with the ligand the cells may be washed one or more times with a suitable buffer to wash away non-specifically bound ligand. Suitable buffers include PBS, any commercially available isotonic buffer or media.

Separation of the ligand bound cells may be achieved by any method known in the art for separating mixtures. For example the ligand may be tagged with a detectable substance as described infra and separation may be achieved by cell sorting using a Fluorescent Activated Cell Sorter (FACS). As another example the ligand may be linked to a solid support as described, infra. The ligand bound cells may be precipitated by gravity. Alternatively an external force may be applied to the ligand bound cells such that the ligand bound cells separate from the other cells comprising the mixed population of cells. For example, the ligand may be linked to a magnetized solid support, such as a magnetic bead and the mixed cell population including the ligand bound cells may be exposed to a magnetic field such that the ligand bound cells separate from the other cells comprising the mixed population of cells.

In other embodiments a cell may be contacted to with one or more ligands that bind specifically to a molecule expressed by a cell considered to be of an extraneous phenotype. In some embodiments the ligand may be conjugated with a chemical agent before it is contacted with the cell. In other embodiments the ligand may be bound to the cell first and then contacted with a chemical agent. Thus, the ligand bound cell may be targeted with a chemical agent that binds to the ligand bound cell, e.g., an agent that binds specifically to the ligand. In some embodiments one or more intervening ligands may be used. Thus a first ligand may bind the cell. A second ligand may bind the first ligand etc. The chemical agent may bind to any of the ligands bound to the cell. The agent may be toxin and its binding to the ligand bound cell may thereby kill the cell. Examples of suitable toxins include diphtheria toxin, tetanus toxin and the like. The agent may be a small molecule, a protein, a peptide, a nucleic acid, a carbohydrate, a lipid. In one embodiment where the ligand is an immunoglobulin the chemical agent may be complement.

Where separation is performed, the extraneous phenotypic cell may be harvested by removal or elution from the ligand. Elution of the extraneous phenotypic cells may be achieved by altering one or more of the binding conditions such as the pH of the buffer containing the bound cells or the salt concentration of the buffer containing the bound cells.

Ligands

Any suitable ligand that binds specifically to a marker expressed by a cell having an extraneous phenotype may be used. The ligand may be comprised of a protein or peptide fragment of a full length protein. Suitable proteins will include proteins or peptides that bind specifically to a molecule expressed on the surface of the extraneous phenotypic cell; however in some embodiments the ligand may bind an intracellular target. The ligand may be also comprised of a nucleic acid, a sugar, a lipid, a glycoprotein, or a lectin or a combination of any of these or a combination of a protein or peptide and any of these. Thus any ligand comprising a specific binding pair may be used as long as it binds specifically to a molecule expressed by the cells comprising the extraneous phenotype and does not bind a target phenotypic cell.

In some embodiments one or more ligands may be used. Thus a first ligand may bind directly to a marker expressed by the extraneous phenotypic cell and a second ligand may then bind to the first ligand. Additional ligands which bind the second or any subsequent ligand are also contemplated. The second (or subsequent) ligand may comprise a tag which facilitates separation of the cells bound to the first ligand according to any method known in the art, e.g. cell sorting by FACS; precipitation of a ligand bound to a solid support; magnetic separation of ligand bound to a magnetic substrate; column chromatography over a ligand linked to a solid support. Of course multiple molecules expressed by an extraphenotypic cell may be bound each with a distinct ligand and each of those ligands in turn may be contacted with one or more additional ligands.

In some embodiments the ligand may be an antibody. Antibody, as used herein, includes an immunoglobulin or a part thereof, and encompasses any polypeptide comprising an antigen binding site regardless of the source, method of production, and other characteristics. The term includes for example, polyclonal, monoclonal, monospecific, polyspecific, humanized, single chain, chimeric, synthetic, recombinant, hybrid, mutated, and CDR grafted antibodies, as well as a molecule comprised of two heavy and two light chains. A part of an antibody can include any fragment which can still bind antigen, for example, an Fab, F(ab')2, Fv, scFv. In some embodiments the antibody may comprise a variable region which binds specifically to an epitope found on an extraneous phenotypic cell and at least a portion of an Fc region to facilitate binding to a solid support or a second ligand. The antibody may be linked to a solid support as described infra. In some embodiments the solid support may be bead. In specific embodiments the bead may be magnetized.

In certain embodiments a suitable ligand may be an antibody to an epitope expressed on the surface of an epithelial cell or an epithelial lineage cell. The epitope may be comprised of proteins, carbohydrates, sugars, and/or lipids expressed on the surface of an epithelial cell. Suitable epitopes may be found on cells expressing one or more of the following molecules: EpCAM; desmocollin, e.g. desmocollin 3; desmoglein, e.g. desmoglein 2; E-cadherin. Thus antibodies which bind to EpCAM, desmocollin, e.g. desmocollin 3, desmoglein, e.g. desmoglein 2, E-cadherin may be suitable ligands to practice the methods described infra. These antibodies may be used alone or in combination with one or more additional ligands. Additional ligands may include ligands that bind specifically to molecules expressed by epithelial cells. Alternatively the ligands may be combined with ligands that bind to one or more molecules expressed by undifferentiated pPS cells. For example antibodies that bind to epitopes found on undifferentiated cells may be used in combination with ligands that bind to cells that express one or more markers found on epithelial cells. Thus examples of suitable antibodies that may be used in the methods for reducing the number of extraneous phenotypic cells in a mixed population may include antibodies to TRA-1-60; TRA-1-81; SSEA 3; SSEA4; (See, Thomson 1998, *Science* 282:1145) Cripto, gastrin-releasing peptide (GRP) receptor, and podocalyxin-like protein (see U.S. patent application Ser. No. 10/388,578) in addition to the ligands that bind to one or more markers expressed by epithelial cells.

The ligand may be coupled or linked covalently or non-covalently with a detectable substance to facilitate identification and/or isolation of bound cells. A detectable substance may include any compound, which when attached to a ligand, permits recognition of the presence of this ligand. The compound can comprise, for example, a radioactive molecule, a fluorescent molecule, a hapten, a carrier, an enzyme, an intervening molecule such as biotin, or a dye. The detectable substance, for example, may be a chemiluminescent material, or a bioluminescent material. The ligand may also be linked with a toxin such as any molecule that induces cell death, cell lysis etc.

In certain embodiments the ligand may be coupled or linked to a solid support. The solid support may comprise a bead, a gel, a monolith or a membrane. The solid support may comprise any material which can be linked to a ligand of interest (e.g., polystyrene, sepharose, sephadex). Solid supports may comprise any synthetic organic polymer such as polyacrylic, vinyl polymers, acrylate, polymethacrylate, polyacrylamide, polyacylonitriles, and polyolefins. Solid supports may also comprise a carbohydrate polymer, e.g., agarose, cellulose, hyaluronic acid, chitin, acyl gellan, dextran, carboxymethylcellulose, carboxymethyl starch, carboxymethyl chitin, poly(actide-co-ethylene glycol). Solid supports may comprise, for example, nitrocellulose, nylon, polyvinylidene fluoride (PVDF) or carboxylated polyvinylidene (U.S. Pat. No. 6,037,124). The solid support may be coated with polyvinyl benzyl dimethyl hydroxyethyl ammonium chloride, polyvinyl benzyl benzoyl aminoethyl dimethyl ammonium chloride, polyvinyl benzyl tributyl ammonium chloride, copolymers of polyvinyl benzyl trihexyl ammonium chloride and polyvinyl benzyl tributyl ammonium chloride, copolymers of polyvinyl benzyl dimethyl ammonium chloride and polyvinyl aminoethyl dimethyl ammonium chloride (U.S. Pat. No. 5,336,596). Solid supports may comprise inorganic oxides, such as silica, zirconia, e.g., carbon clad zirconia (U.S. Pat. No. 5,182,016), titania, ceria, alumina, manganese, magnesia (i.e., magnesium oxide), calcium oxide, controlled pore glass (CPG). Solid supports may also comprise combinations of some of the above-mentioned supports including, but not limited to, dextran-acrylamide. A solid support may be prepared to minimize non-specific interactions e.g., by coating it with one or more blocking proteins such as albumin, casein and the like.

In some embodiments the ligand may be linked to both a solid support and a detectable substance.

In some embodiments about the ligand may be linked to a solid support such as a bead by mixing a suitable concentration of ligand and beads under conditions that facilitate covalent binding of the ligand to the solid support. Suitable concentrations of ligand and beads range from about 0.1 mg of ligand/mL of beads to about 20 mg of ligand/mL of bead; from about 0.5 mg of ligand/mL of beads to about 10 mg of ligand/mL of bead; from about 1.0 mg of ligand/mL of beads to about 5 mg of ligand/mL of bead. In some embodiments about 1 mg of ligand/mL of bead may be used. In other embodiments about 2 mg of ligand/mL of bead may be used. In some embodiments about 3 mg of ligand/mL of bead may be used. In other embodiments about 4 mg of ligand/mL of bead may be used. In other embodiments about 5 mg of ligand/mL of bead may be used.

In some embodiments an antibody may be linked directly to the bead using known conjugation chemistry such as the formation of EHS ester. In other embodiments a specific binding partner of the antibody may be linked directly to the bead and the antibody in turn may bind to the specific binding partner thus linking it to the bead. The specific binding partner may bind to a region of the antibody that does not bind its specific epitope, e.g., a non variable region of the antibody. A suitable region may include the Fc region of the antibody. Examples of binding partners that bind to the Fc region of an antibody include protein A and protein G. Alternatively, the antibody may be conjugated to another molecule such as biotin and then coupled to a bead conjugated with streptavidin.

In one specific embodiment the ligand is an antibody to EpCAM linked, e.g., covalently to a bead such as a magnetic bead. The antibody may be directly linked to the bead or indirectly linked by an intervening molecule such as protein A, protein G, biotin, streptavidin as described in the previous paragraph. Alternatively, a short linker may serve to anchor the antibody to the bead thereby enhancing binding accessibility of the antibody. The linker may be comprised of one or more amino acids for example.

In another specific embodiment the ligand may be an antibody to TRA-1-60 linked covalently, e.g., to a bead such as a magnetic bead. The antibody may be directly linked to the bead or indirectly linked by an intervening molecule such as protein A, protein G, biotin, streptavidin as described in the previous paragraph. Alternatively a short linker may serve to anchor the antibody to the bead thereby enhancing binding accessibility of the antibody. The linker may be comprised of one or more amino acids for example. The antibody to TRA-1-60 may have an IgG isotype in some embodiments. In other embodiments the antibody to TRA-1-60 may have an IgM isotype.

In some embodiments a combination of one or more antibodies to markers expressed by epithelial cells may be used to deplete extraneous phenotypic cells from a mixed population of cells. In some embodiments the one more antibodies to markers expressed by epithelial cells may be combined with one or more antibodies to markers expressed by undifferentiated cells.

In some embodiments a combination of one or more antibodies to EpCAM and one or more antibodies to TRA-1-60 may be used to deplete extraneous phenotypic cells from a mixed population of cells. In some embodiments all of the antibodies used may have an IgG isotype. In other embodiments at least one of the antibodies may have an IgG isotype. In still other embodiments at least one of the antibodies may have an IgM isotype.

Cell Populations

In certain embodiments the invention provides a mixed population of cells that is enriched for a targeted phenotype. The mixed population of cells may be enriched for a targeted cell type by eliminating at least one cell having an extraneous phenotype from the mixed population of cells.

1. Extraneous Phenotypes

In some embodiments extraneous phenotypic cells may include for example a cell having an epithelial morphology, a cell expressing at least one marker expressed in or on an epithelial cell, a cell capable of forming an clustered epithelial structure when implanted into a subject, an undifferentiated pluripotent cell, a cell having the morphology of an undifferentiated cell, a cell expressing at least one marker expressed in or on undifferentiated cells. Examples of markers expressed in or on undifferentiated TRA-1-60, TRA-1-81; SSEA 3; SSEA 4; Oct 4. Examples of markers expressed in or on epithelial cells include EpCAM, and cytokeratin. Other suitable markers expressed on epithelial cells may include desmocollin, desmoglein, and E-cadherin. These cells may have the capacity to form epithelial clusters when implanted into a subject such as a rodent.

2. Targeted Phenotypes

Targeted phenotypic cells may be the in vitro differentiated progeny of pPS cells and may include any of the following: oligodendrocytes, neural cells such as neurons and astrocytes, cardiomyocytes, hematopoietic cells, pancreatic islet cells, hepatocytes, osteoblast and chondrocytes. In some embodiments the target cell may be a mature target cell such as a mature cardiomyocyte, a mature oligodendrocyte, etc. In other embodiments the targeted cell type may a precursor cell such as a cardiomyocyte precursor, an oligodendrocyte precursor, a neural cell precursor, an islet cell precursor, a hematopoietic cell precursor, a hepatocyte precursor, an osteoblast precursor, a chondrocyte precursor. Precursor cells may express one or more markers expressed by a corresponding mature cell type; and/or have one or more morphological features found on the corresponding mature cell types and/or have the ability to differentiate into the corresponding mature cell type either in vivo or in vitro. Targeted cell types may include cells that express one or more markers expressed on, in or by one of the following cell types: oligodendrocytes, neuronal cells cardiomyocytes, hematopoietic cells, pancreatic islet cells, hepatocytes, osteoblasts and chondrocytes (examples of suitable markers are provided in the paragraphs that follow). Markers may be detected using any method known in the art, for example immunocytochemistry, immunohistochemistry, FACS, western blot, ELISA, or qPCR may be used to detect one or more markers expressed on, in or by a target cell.

Methods of differentiating pPS cells in vitro into oligodendrocytes have been described in U.S. Pat. No. 7,285,415, which is hereby incorporated by reference in its entirety. Oligodendrocytes may be differentiated in vitro from a population of pPS cells for example by contacting the pPS cells with a growth factor, a ligand to a thyroid hormone receptor and a ligand for a retinoic acid receptor. Markers expressed on, in or by oligodendrocytes include NG2, a chondroitin sulfate proteoglycan expressed by macrophages and oligodendrocyte progenitors; galactocerebroside (GalC), a marker for committed oligodendrocytes; myelin basic protein (MBP), a marker of mature myelin; microtubule associated protein 2 (MAP-2), a marker for CNS cells; myelin proteolipid protein, a component of myelin that is expressed on oligodendrocytes and glial precursors; the epitope defined by the O4 antibody, a marker for oligodendrocytes, astrocytes, and their precursors; A2B5, an epitope expressed on type 2 astrocytes, glial progenitors, and oligodendrocyte progenitors; the epitope recognized by RIP antibody, which stains oligodendrocytes and their processes, and coincides with myelinated axons in both the spinal cord and the cerebellum.

Methods of differentiating pPS cells in vitro into neural cells have been described, see, e.g., U.S. Pat. No. 6,833,269; U.S. Patent Publication Nos. 2005/0095707; 2005/0158855, all of which are incorporated by reference in their entirety. Neural cells may be differentiated in vitro from a population of PS cells for example by contacting the pPS cells with noggin and/or follistatin; by contacting the pPS cells with a TGF β antagonist or by forming embryoid bodies (EBs) and culturing the EBs in suspension with 10 μM retinoic acid, then plating the cells into defined medium supplemented with epidermal growth factor (EGF), fibroblast growth factor (bFGF), platelet derived growth factor (PDGF), and insulin like growth factor 1 (IGF-1). Markers expressed on, in or by neural cells include NCAM, A2B5, β tubulin III, and microtubule-associated protein 2 (MAP 2).

Methods of differentiating pPS in vitro into cardiomyocytes have been described, see, e.g., U.S. Pat. Nos. 7,452,718; 7,425,448; U.S. Patent Publication Nos. 2005/0054092; 2007/0010012, all of which are hereby incorporated by reference in their entirety. pPS cells may be contacted with activin followed by bone morphogenic protein (BMP) to differentiate pPS cells into cardiomyocytes. Markers expressed on, in or by cardiomyocytes include cardiac troponin I (cTnI), a subunit of troponin complex that provides a calcium sensitive molecular switch for the regulation of striated muscle contraction; cardiac troponin T (cTnT); Nkx2.5, a cardiac transcription factor expressed in cardiac mesoderm during early embryonic development, which persists in the developing heart; atrial natriuretic factor (ANF), a hormone expressed in developing heart and fetal cardiomyocytes but down-regulated in adults. Other suitable markers include myosin heavy chain (MHC), particularly the β chain which is cardiac specific; titin, tropomyosin, α sarcomeric actinin, and desmin; GATA-4, a transcription factor that is highly expressed in cardiac mesoderm and persists in the developing heart. Yet other suitable markers may include MEF 2A, MEF 2B, MEF 2C, MEF 2D; N-cadherin, which mediates adhesion among cardiac cells; connexin 43, which forms the gap junction between cardiomyocytes; β1 adrenoceptor (β1 AR); creatine kinase MB (CK MB) and myoglobin, which are elevated in serum following myocardial infarction; α cardiac actin.

Methods of differentiating pPS cells in vitro into hematopoietic cells have been described see, e.g., U.S. Pat. No. 7,247,480; U.S. patent application Ser. No. 12/412,480 and U.S. Patent Publication No. 2005/0282272, all of which are hereby incorporated by reference in their entirety. As an example pPS cells may be differentiated into dendritic cells by contacting the pPS cells with a plurality of cytokines such as BMP-4, granulocyte macrophage colony stimulating factor (GM-CSF), stem cell factor (SCF) and vascular endothelial growth factor (VEGF) to differentiate the pPS cells into immature dendritic cells. The immature dendritic cells may then be contacted with a maturation cocktail e.g., GM-CSF, tumor necrosis factor α (TNFα), interleukin 1-β (IL-1β), interferon γ (IFNγ), and prostaglandin E2 (PGE2) to generate mature dendritic cells. Markers expressed in on or by hematopoietic cells include CD34, CD59, Thy1/CD90, CD38, C-kit/CD117, CD13, IL-3Rα (CD123), and CD45RA, CD64 CD14, CD45, CD11a, CD11b, CD15 CD11c, MHC I, MHC II, CD83, CCR7, CD205, CD86, CD40, MHC I, MHC II, CD8, CD4, CD119, CD74, CD71, CD75, CD51, CD56, CD65, CD10, CD66a, CD66b, CD44, betaglobin and myoglobin.

Methods of differentiating pPS cells in vitro into islet cells have been described, see, e.g., U.S. Pat. No. 7,033,831 and U.S. patent application Ser. No. 12/303,895, both of which are incorporated by reference in their entirety. As an example pPS cells may be differentiated into islet cells by first contacting the pPS cells with activin and sodium butyrate followed by noggin, fibroblast growth factor (FGF), epidermal growth factor (EGF), insulin like growth factor 2 (IGF-2) and nicotinamide. Markers expressed in on or by islet cells (including islet cell precursors) include insulin, c-peptide, Hlxb9, Pdx1, Neurogenin3, Pax4, NeuroDI, Isl1, Nkx2.2, and Nkx6.1; pancreatic polypeptide, islet amyloid polypeptide (IAPP), Islet 1, Beta 2/NeuroD, HNF4a. Also included are definitive endoderm cells, a particular islet precursor cell that express Sox17 and HNF3β.

Methods of differentiating pPS cells in vitro into hepatocytes have been described, see, e.g., U.S. Pat. Nos. 6,458,589; 6,506,574; 7,256,042; 7,473,555; and U.S. patent application Ser. No. 12/303,104, all of which are incorporated by reference in their entirety. For example pPS cells may be differentiated in vitro into hepatocytes by contacting the pPS cells with DMSO and butyrate followed by EGF, TGF-α, hepatocyte growth factor (HGF), and butyrate. Markers expressed in on or by hepatocytes include $α_1$-antitrypsin (AAT), albumin; asialoglycoprotein receptor (either the ASGR-1 or ASGR-2 isotype); Ck8, Ck18, Ck19, cytochrome p450, CYP1A1/2d CYP2A6 CYP2B6, CYP2C9, CYP2E1, CYP3A3-5 glucose-6-phosphatase; HNF-4α, α-fetoprotein, apoE, glucokinase, insulin like growth factors 1 and 2 receptor, insulin receptor, leptin, apoAI, apoAII, apoB, apoCIII, apoCII, aldolase B, phenylalanine hydroxylase, L-type fatty acid binding protein, transferrin, retinol binding protein, erythropoietin (EPO), and NADPH-Cc.

Methods of differentiating pPS cells in vitro into osteoblasts have been described, see, e.g., U.S. Patent Application No. 2005/028274, which is incorporated by reference in its entirety. For example pPS cells may be differentiated in vitro into osteoblasts by contacting the pPS cells with bone morphogenic protein (BMP), a ligand for the human TGF-β receptor, or a ligand for the vitamin D receptor. The cells may also be contacted with dexamethasone, ascorbic acid-2-phosphate, and sources of calcium and phosphate. Markers expressed in on or by osteoblasts include osteocalcin, osteonectin, type 1 collagen, alkaline phosphatase, BMP receptors, PTH receptors, CD105 (endoglin), CD106 (VCAM), CD166 (ALCAM), CD29, CD44 and GATA 4.

Methods of differentiating pPS cells in vitro into chondrocytes have been described, see, e.g., U.S. Patent Application No 2006/0148077. For example pPS cells may be differentiated in vitro into chondrocytes by contacting the pPS cells with transforming growth factors (TGF), fibroblast growth factors (FGF), growth and differentiation factors (GDF), bone morphogenic proteins (BMP), hedgehog proteins (HH), L-ascorbic acid, and parathyroid hormone-related protein (PTHrP). The cells may be maintained in culture during the differentiation process as a micromass. Markers express in on or by chondrocytes include Type II collagen or aggrecan.

Enriched Cell Populations

As discussed above the invention provides cell populations enriched for a target phenotype. The cell populations may be enriched by reducing the number of extraneous phenotypic cells from the mixed population of cells. The extraneous phenotypic cell may express one or more markers expressed by epithelial cells as discussed infra. The extraneous phenotypic cells may have the morphology of epithelial cells. The extraneous phenotypic cells may have the capability of forming a clustered epithelial structure when implanted into a subject. The extraneous phenotypic cells may be undifferentiated pPS cells. The extraneous phenotypic cells may be cells that express one or more markers expressed by a pPS cell, e.g., TRA-1-60, TRA-1-81, Oct4, SSEA3, SSEA4. The extraneous phenotypic cells may comprise a combination of one or more of the extraneous phenotypic cells described in this paragraph. Thus in certain embodiments the invention provides enriched populations of cell comprising a targeted phenotype wherein at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% of the extraneous phenotypic cells have been removed from the cell population comprising the target cell phenotype.

In other embodiments the invention provides a mixed cell population comprising a targeted phenotype, wherein at least one cell having an extraneous phenotype has been removed from the mixed population, and wherein the target phenotype comprises at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, of the cells in the population after the at least one cell having an extraneous phenotype has been removed. The targeted cell type may be chosen from oligodendrocytes, neural cells, cardiomyocytes, hematopoietic cells, pancreatic islet cells, hepatocytes, osteoblast and chondrocytes or from a cell that expresses one or more markers expressed on, in or by a cell chosen from oligodendrocytes, neuronal cells, cardiomyocytes, hematopoietic cells, pancreatic islet cells, hepatocytes, osteoblast and chondrocytes.

Kits

In certain embodiments the invention provides a kit for depleting cells having an extraneous phenotype from a mixed population of cells wherein the mixed population of cells comprises a targeted phenotypic cell and extraneous phenotypic cells. Both cell types may be the in vitro progeny of pPS cells. For example the targeted phenotypic cells may be comprised of the in vitro differentiated progeny of the pPS cells while the extraneous phenotypic cells may comprise differentiated progeny of the pPS cells, undifferentiated progeny of the pPS cells or a combination of both. The kit may comprise one or more ligands that specifically bind to one or more molecules expressed by the cells comprising the extraneous phenotype. The one or more ligands may be provided in one or more containers. The ligands may be provided in a solution such as an aqueous buffer, e.g., an isotonic buffer, PBS or the like. Alternatively the one or more ligands may be provided in lyophilized form. The kit may include instructions for reconstituting the lyophilized ligand. The kit may include instructions for contacting the mixed population of cells with the ligand. The instructions may include a suitable concentration of ligand to use to deplete the extraneous phenotype. Optionally the kit may comprise one or more controls, e.g., a positive control cell type that will bind to the one or more ligands provided and a negative control cell type that will not bind to the one or more provided ligands.

In some embodiments the ligand provided in the kit may be an antibody. The ligand may be an antibody that binds to a molecule expressed by a cell comprising the extraneous phenotype. Examples of suitable antibodies include a TRA-1-60 antibody, an EpCAM antibody, a cytokeratin antibody such as a pan-cytokeratin antibody, an antibody to TRA-1-81, an antibody to SSEA3, and an antibody to SSEA4. The antibody may be any isotype e.g., IgG, IgM, IgA, IgE, IgD. In one embodiment the antibody may be an IgG that binds to EpCAM. In one embodiment the antibody may be an IgG that binds to a cytokeratin. In one embodiment a plurality of IgG antibodies binding to different epitopes on a plurality of cytokeratins may be used. In one embodiment the antibody may be an IgM that binds to TRA-1-60. In one embodiment the antibody may be an IgG that binds to TRA-1-60. In one embodiment a combination of different antibodies may be used, e.g., a plurality of the types of antibodies described in this paragraph. Thus a plurality of antibodies directed to a single antigen (but different epitopes) may be used. A plurality of antibodies directed to a plurality of antigens may be used.

The kit may comprise a solid support for the ligand. Solid supports are described in detail infra. The ligand may be provided already linked to the solid support in a single container. Alternatively the kit may provide the antibody and solid support unlinked to one another. The solid support and the ligand may thus be provided in separate containers. The kit may provide instructions and one or more reagents for linking the ligand to the solid support.

The kit may further comprise one or more detectable substances which may be linked to the one or more ligands provided in the kit. Detectable substances are described in detail infra. The one or more detectable substances may each be provided in one or more separate containers along with instructions for linking the one or more detectable substances to the one or more ligands.

The kit may provide a means for applying an external force to the mixed population of cells after it has been contacted with the ligand bound to a solid support such that separation of the ligand bound extraneous phenotypic cells from the mixed population of cells is facilitated. The external force may be a magnetic field.

In one embodiment the kit may comprise one or more antibodies chosen from an antibody to EpCAM, an antibody to cytokeratin, e.g., pan-cytokeratin, an antibody to desmocollin, an antibody to desmoglein, and an antibody to E-cadherin and/or an antibody to TRA-1-60. The one or more antibodies may be conjugated to a magnetic bead. The kit may further comprise a magnetic field source adapted to facilitate removal of the extraneous phenotypic cells bound to the antibodies. The kit may comprise one or more containers to hold the one or more antibodies and the source of the magnetic field. The kit may optionally include wash solutions and/or buffers and instructions for using the antibodies and the magnetic field.

Uses of Enriched Cell Populations

This invention provides a method to produce large numbers of cells enriched for a target phenotype. Target phenotypes include oligodendrocytes, neural cells, cardiomyocyte, hematopoietic cells, islet cells, hepatocytes, chondrocytes and osteoblasts. These cell populations can be used for a number of important research, development, and commercial purposes. Because the populations provided are enriched for a target phenotype they will be more suitable for all of the uses described infra when compared to cell populations that have not been so enriched.

Screening

The enriched target cell populations of this invention can be used commercially to screen for factors (such as solvents, small molecule drugs, peptides, oligonucleotides) or environmental conditions (such as culture conditions or manipulation) that affect the characteristics of such cells and their various progeny. Characteristics may include phenotypic or functional traits of the cells.

Other screening applications of this invention relate to the testing of pharmaceutical compounds for their effect on enriched target cell populations. Screening may be done either because the compound is designed to have a pharmacological effect on the cells, or because a compound designed to have effects elsewhere may have unintended side effects on cells of the target phenotype. Other screening applications could include screening compounds for carcinogenic or other toxic effects. The screening can be conducted using any of the precursor cells or terminally differentiated/mature cells of the invention in order to determine if the target compound has a beneficial or harmful effect on the target cell. Using the enriched target populations described infra will provide for more accurate screening results.

The reader is referred generally to the standard textbook *In vitro Methods in Pharmaceutical Research*, Academic Press, 1997. Assessment of the activity of candidate pharmaceutical compounds generally involves combining the enriched target cells of this invention with the candidate compound, either alone or in combination with other drugs. The investigator determines any change in the morphology, marker phenotype as described infra, or functional activity of the cells, that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in *In vitro Methods in Pharmaceutical Research*, Academic Press, 1997) for further elaboration.

Where an effect is observed, the concentration of the compound can be titrated to determine the median effective dose ($ED_{50}$).

Animal Testing

This invention also provides for the use of enriched target cells of the invention to enhance tissue maintenance or repair of tissue function for any perceived need, such as an inborn error in metabolic function, the effect of a disease condition, or the result of significant trauma.

To determine the suitability of cell compositions for therapeutic administration, the enriched target cells can first be tested in a suitable animal model such as a rat, mouse, guinea pig, rabbit, cow, horse, sheep, pig, dog, primate or other mammal. At one level, cells are assessed for their ability to survive and maintain their phenotype in vivo. Cell compositions may be administered to immunodeficient animals (such as nude mice, or animals rendered immunodeficient chemically or by irradiation). Tissues are harvested after a period of regrowth, and assessed as to whether pluripotent stem derived cells are still present. Functional tests as are known in the art may be performed.

Cell survival may be monitored by administering cells that express a detectable label (such as green fluorescent protein, or β-galactosidase); that have been prelabeled (for example, with BrdU or [$^3$H]thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

In one embodiment the enriched target cell populations may be administered to an animal to test for the formation of clustered epithelial structures. The animal may be a rodent such as a mouse or a rat. The enriched cells may be administered to the animal for a suitable length of time, e.g., about 1-12 months. The animal may be sacrificed and the tissue receiving the enriched cell population may be subjected to histological examination or ICC or both to screen for primate cells having epithelial morphology and/or labeling for one or more markers found on an epithelial cell and/or one or more markers found on an undifferentiated pPS cell.

In other embodiments the enriched target cells of the invention may be tested functionally using a known animal model for a particular disease. If the target cell type is a cardiomyocyte, for example, one of several models for heart disease and or infarction can be used. Hearts can be cryoinjured by placing a precooled aluminum rod in contact with the surface of the anterior left ventricle wall (Murry et al., *J. Clin. Invest.* 98:2209, 1996; Reinecke et al., *Circulation* 100:193, 1999; U.S. Pat. No. 6,099,832; Reinecke et al., *Circ Res.*, Epub March 2004). In larger animals, cryoinjury can be effected by placing a 30-50 mm copper disk probe cooled in liquid $N_2$ on the anterior wall of the left ventricle for ~20 min (Chiu et al., *Ann. Thorac. Surg.* 60:12, 1995). Infarction can be induced by ligating the left main coronary artery (Li et al., *J. Clin. Invest.* 100:1991, 1997) or by using an ameroid constriction device that gradually swells to occlude an artery. Injured sites are treated with cell preparations of this invention, and the heart tissue is examined by histology for the presence of the cells in the damaged area. Cardiac function can be monitored by determining such parameters as left ventricular end-diastolic pressure, developed pressure, rate of pressure rise, and rate of pressure decay.

Where the target cell is an oligodendrocyte, regions of chronic demyelination may be induced in the adult rat dorsal column (Keirstead et al., *J. Neurosci.* 19:7529, 1999). The spinal cord may be exposed to 40 G of X irradiation over a distance of 2 cm centered on T9 using lead shielding, which introduces nicks into the DNA of exposed cells, thus causing death of the cells that are dividing. This is followed by direct intraspinal injection of ethidium bromide 2 days later at T9. Ethidium bromide is a DNA interchelating agent that kills cells exposed to it, rendering an acellular region of chronic demyelination that is free of viable oligodendrocytes and astrocytes through ~60% of the area of the dorsal column.

Three days later, the animals receive transplants of enriched populations of oligodendrocyte lineage cells into the site of demyelination. Optionally, the cells can be prelabeled with bromodeoxyuridine (BrdU) added to the culture medium 48 hours in advance. In the first instance, cells can be prepared as clusters of ~30 precursors, concentrated to a density of ~60,000 cells per μL. One μL of cells is administered into the injury site using a pulled glass micropipette or syringe needle of about 80 um outside diameter over a period of about 10 minutes. After about 2-4 weeks, tissue samples are prepared for resin or cryostat sectioning into 1 mm transverse blocks.

Sections from the coronal face are stained with toluidine blue and analyzed for general pathology, evidence of remyelination, and cell morphology. Since the damaged regions are acellular, cells present after transplantation are derived from the administered cells. Cryostat sections can be stained for markers of relevant cell types, such as GFAP (astrocytes), CNP (oligodendrocytes), RIP (oligodendrocytes), or NeuN (neurons). Ultrathin sections can also be analyzed by electron microscopy for the number of myelin lamellae and cellular ultrastructure. Redistribution of transplanted cells throughout areas demyelination, and differentiation into mature myelinating cells can be determined. Remyelination as a percentage of demyelinated axons at a level of 25%, 50%, or 75% is evidence of increased biological efficacy.

The enriched target cells can be tested in a model for SCI including contusion injuries and dorsal hemisection. For contusion injuries, the spinal course is displaced for about 0.9 mm (moderate injury) over 23 milliseconds using a suitable spinal contusion injury device. For hemisection injuries, the dorsal half of the spinal cord is cut with a pointed scalpel blade using a stereotactic manipulator. Both procedures are followed by suitable postoperative care. To promote migration of implanted cells and remove myelin-associated growth inhibitors, the spinal cord may optionally also be demyelinated (Keirstead et al., *Exp Neurol.* 151:303, 1998). A 2 mm hole is produced in the center of the vertebra canal and caudal to the site of axonal injury. The exposed spinal cord is the injected with about 4 µL polyclonal anti GalC antibody (Millipore Corp., Billerica, Mass.) at a dilution of 1:2 with 33% guinea pig complement (Harlan SeraLab, San Francisco, Calif.) in phosphate buffered saline.

The animals are transplanted with enriched target phenotype oligodendrocyte lineage cells about 24 hours after injury through a pulled glass micropipette or syringe needle. Alternatively, a chronic injury model can be created by withholding treatment after injury for 1-3 months. Following treatment with the cells, functional response can be recorded by video tape, and monitored on a regular basis for evidence of clinical improvement. For example, overground locomotion can be quantitated using the BBB scale, a 21-point scale based on joint movements, weight support, limb coordination, and other features.

Therapeutic Use in Humans

After adequate testing, enriched target cells of this invention can be used for tissue reconstitution or regeneration in a human patient or other subject in need of such treatment. The cells are administered in a manner that permits them to graft or migrate to the intended tissue site and reconstitute or regenerate the functionally deficient area. Thus enriched target cell populations comprising cardiomyocytes may be administered to the heart. Enriched target cell populations comprising oligodendrocytes may be administered to the spinal cord. Enriched target cell populations comprising hepatocytes may be administered to the liver. Enriched target cell populations comprising hematopoietic cells may be administered intravenously. Enriched populations of cells comprising islet cells may be administered near the kidney or pancreas. Alternatively, the enriched population of cells comprising islet cells may be administered subcutaneously in an implantable device that shields the cells from an auto-immune response. Enriched populations of cells comprising chondrocytes may be administered to a joint that is deficient in cartilage or in need of cartilage repair. Enriched populations of osteoblasts may be administered to a fractured bone.

Administration of the population of cells may be achieved by any method known in the art. For example the cells may be administered surgically directly to the organ or tissue in need of a cellular transplant. Alternatively non-invasive procedures may be used to administer the cells to the subject. Examples of non-invasive delivery methods include the use of syringes and/or catheters to deliver the cells into the organ or tissue in need of cellular therapy.

The patient receiving an allograft of enriched target cells of the invention may be treated to reduce immune rejection of the transplanted cells. Methods contemplated include the administration of traditional immunosuppressive drugs like tacrolimus, cyclosporin A (Dunn et al., *Drugs* 61:1957, 2001), or inducing immunotolerance using a matched population of pluripotent stem derived cells (WO 02/44343; U.S. Pat. No. 6,280,718; WO 03/050251). Alternatively a combination of anti-inflammatory (such as prodnisone) and immunosuppressive drugs may be used.

The enriched target cells of this invention can be supplied in the form of a pharmaceutical composition, comprising an isotonic excipient prepared under sufficiently sterile conditions for human administration. To reduce the risk of cell death upon engraftment, the cells may be treated by heat shock or cultured with ~0.5 U/mL erythropoietin ~24 hours before administration.

For general principles in medicinal formulation, the reader is referred to *Cell Therapy: Stem Cell Transplantation, Gene Therapy, and Cellular Immunotherapy*, by G. Morstyn & W. Sheridan, Eds., Cambridge University Press, 1996; and *Hematopoietic Stem Cell Therapy*, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the enriched target cells. Suitable ingredients will vary depending on the target phenotype but may include matrix proteins that support or promote adhesion of the target cell type or that promote vascularization of the implanted tissue.

This invention also includes a reagent system, comprising a set or combination of cells that exist at any time during manufacture, distribution, or use. The cell sets comprise any combination of two or more cell populations described in this disclosure, exemplified but not limited to a type of differentiated pluripotent stem-derived cell, in combination with undifferentiated primate pluripotent stem cells or other differentiated cell types, often sharing the same genome. Each cell type in the set may be packaged together, or in separate containers in the same facility, or at different locations, at the same or different times, under control of the same entity or different entities sharing a business relationship.

Pharmaceutical compositions of this invention may optionally be packaged in a suitable container with written instructions for a desired purpose, such as the reconstitution of cardiomyocyte-lineage cell function to improve a disease condition or abnormality of the cardiac muscle or remyelination of an injured spinal cord.

The enriched target cells of this invention can be used to prepare a cDNA library relatively uncontaminated with cDNA preferentially expressed in cells from other lineages. For example, enriched target cells are collected by centrifugation at 1000 rpm for 5 minutes, and then mRNA is prepared and reverse transcribed. Expression patterns of the enriched target cells may be compared with other cell types by microarray analysis, reviewed generally by Fritz et al. *Science* 288:316, 2000. Such libraries would be especially well suited for studying gene expression in target cells compared to the undifferentiated pPS cells from which they were derived. Because these cells share essentially identical genomes comparisons in gene expression using for example subtractive hybridization can be made with little or no background noise. Reducing the number of extraneous phenotypic cells within a cell population will provide improved signal to noise ratios in comparing gene expression in two populations of cells, e.g., differentiated target progeny and the parent pPS cell line giving rise to the differentiated target cells.

The differentiated cells of this invention can also be used to prepare antibodies that are specific for markers of the enriched target cells. Polyclonal antibodies can be prepared by injecting a vertebrate animal with cells of this invention in an immunogenic form. Production of monoclonal antibodies is described in such standard references as Harlow & Lane (1988) *Antibodies: A Laboratory Manual*, U.S. Pat. Nos. 4,491,632, 4,472,500 and 4,444,887, and *Methods in Enzymology* 73B:3 (1981).

Primate Pluripotent Stem Cells

The present invention provides methods for enriching target cells differentiated in vitro from pPS cells. pPS cells include any primate pluripotent cell. A pluripotent cell will, under appropriate growth conditions, be able to form at least one cell type from each of the three primary germ layers: mesoderm, endoderm and ectoderm. The pPS cells may originate from pre-embryonic, embryonic or fetal tissue or mature differentiated cells. Typically, the pPS cells are not derived from a malignant source. pPS cells will form teratomas when implanted in an immuno-deficient mouse, e.g., a SCID mouse. The pPS cells may be obtained from an established cell line. Established cell lines are available from public cell banks such as WiCell and the UK Stem Cell Bank.

Under the microscope, pPS cells appear with high nuclear/cytoplasmic ratios, prominent nucleoli, and compact colony formation with poorly discernable cell junctions. pPS cells typically express the stage-specific embryonic antigens (SSEA) 3 and 4, and markers detectable using antibodies designated TRA-1-60 and TRA-1-81. Undifferentiated human embryonic stem cells also typically express the transcription factor Oct-3/4, Cripto, gastrin-releasing peptide (GRP) receptor, podocalyxin-like protein (PODXL), nanog and telomerase reverse transcriptase, e.g., hTERT (US 2003/0224411 A1), as detected by RT-PCR.

pPS cells that may be used in any of the embodiments of the invention include, but are not limited to, embryonic stem cells such as human embryonic stem cells (hES). Embryonic stem cells used in the invention may be chosen from embryonic stem cell lines. A large number of embryonic stem cell lines have been established including, but not limited to, H1, H7, H9, H13 or H14 (Thompson, (1998)*Science* 282:1145); hESBGN-01, hESBGN-02, hESBGN-03 (BresaGen, Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., (2005) *Fertil. Steril.* 83(5):1517); lines HUES 1-17 (Cowan et al., (2004) *NEJM* 350(13):1353); and line ACT-14 (Klimanskaya et al., (2005) Lancet, 365(9471): 1636).

Other primate pluripotent stem cell types include, but are not limited to, primitive ectoderm-like (EPL) cells, described in WO 01/51610 and human embryonic germ (hEG) cells (Shamblott et al., (1998) *Proc. Natl. Acad. Sci. USA* 95:13726).

pPS cells suitable for use in any of the embodiments of the invention also include induced primate pluripotent stem (iPS) cells. iPS cells refer to cells that are genetically modified, e.g., by transfection with one or more appropriate vectors, such that they attain the phenotype of a pPS cell (Takahashi et al. (2007) *Cell* 131(5):861; Yu et al. (2007) *Science* 318:1917). Alternatively, iPS cells may be obtained by reprogramming adult cells by contacting them with a protein cocktail that induces the cells to reprogram such that they have phenotypic and morphological traits associated with blastocyst derived pluripotent stem cells see, Kim et al. (2009) *Cell Stem Cell* 4(6):472. Phenotypic traits attained by these reprogrammed cells include morphology resembling pluripotent stem cells isolated from a blastocyst, as well as expression of surface antigens, gene expression and telomerase activity found in pPS cells. The iPS cells may have the ability to differentiate into at least one cell type from each of the primary germ layers: ectoderm, endoderm and mesoderm. The iPS cells may also form teratomas when injected into immunodeficient mice, e.g., SCID mice. (Takahashi et al., (2007) *Cell* 131(5): 861; Yu et al., (2007) *Science* 318:1917).

Culture Conditions for Primate Pluripotent Stem Cells

In certain embodiments, pPS cells used in the present invention may have been derived in a feeder-free manner (see, e.g., Klimanskaya et al., (2005) *Lancet* 365(9471):1636). In certain embodiments the pPS may be cultured prior to use in a serum free environment.

pPS cells may be cultured using a variety of substrates, media, and other supplements and factors known in the art. In some embodiments a suitable substrate may be comprised of a matrix including one or more of the following: laminin, collagen, fibronectin, vitronectin, heparin sulfate proteoglycan. In some embodiments the matrix may comprise a soluble extract of the basement membrane from a murine EHS sarcoma which is commercially available as Matrigel™ (BD Biosciences, San Jose, Calif.). In other embodiments the matrix may comprise one more isolated matrix proteins of human, humanized, or murine origin, e.g., CELLstart™ (Invitrogen, Carlsbad, Calif.). In still other embodiments a suitable substrate may be comprised of one or more polymers such as one or more acrylates. The polymers may include one or more proteins or peptide fragments derived from a protein found in vivo in the extra-cellular matrix. In one particular embodiment the substrate is comprised of one or more acrylates and a conjugated vitronectin peptide (see, e.g. U.S Patent Publication No. 2009/0191633; U.S Patent Publication No. 2009/0191626; U.S Patent Publication No. 2009/0203065). pPS cells can be propagated continuously in culture, using culture conditions that promote proliferation while inhibiting differentiation.

Exemplary medium may be made with 80% DMEM (such as Knock-Out DMEM, Gibco), 20% of either defined fetal bovine serum (FBS, Hyclone) or serum replacement (US 2002/0076747 A1, Life Technologies Inc.), 1% non-essential amino acids, 1 mM L-glutamine, and 0.1 mM 3-mercaptoethanol. Other suitable media include serum free defined media such as X-VIVO™10 (Lonza, Walkersville, Md.). Still other commercially available media formulations that may be used in certain embodiments of the invention include X-VIVO™15 (Lonza, Walkersville, Md.); mTeSR™ (Stem Cell Technologies, Vancouver, Calif.); hTeSR™ (Stem Cell Technologies, Vancouver, Calif.), StemPro™ (Invitrogen, Carlsbad, Calif.) and Cellgro™ DC (Mediatech, Inc., Manassas, Va.).

In certain embodiments, pPS cells may be maintained in an undifferentiated state without added feeder cells (see, e.g., (2004) Rosier et al., *Dev. Dynam.* 229:259). Feeder-free cultures are typically supported by a nutrient medium containing factors that promote proliferation of the cells without differentiation (see, e.g., U.S. Pat. No. 6,800,480). In certain embodiments, conditioned media containing such factors may be used. Conditioned media may be obtained by culturing the media with cells secreting such factors. Suitable cells include irradiated (~4,000 rad) primary mouse embryonic fibroblasts, telomerized mouse fibroblasts, or fibroblast-like cells derived from pPS cells (U.S. Pat. No. 6,642,048).

Medium can be conditioned by plating the feeders in a serum free medium such as KO DMEM supplemented with 20% serum replacement and 4 ng/mL bFGF. Medium that has been conditioned for 1-2 days may be supplemented with further bFGF, and used to support pPS cell culture for 1-2 days (see. e.g., WO 01/51616; Xu et al., (2001) *Nat. Biotechnol.* 19:971).

Alternatively, fresh or non-conditioned medium can be used, which has been supplemented with added factors (like a fibroblast growth factor or forskolin) that promote proliferation of the cells in an undifferentiated form. Exemplary is a base medium like X-VIVO™ 10 (Lonza, Walkersville, Md.) or QBSF™-60 (Quality Biological Inc. Gaithersburg, Md.), supplemented with bFGF at 40-80 ng/mL, and optionally containing SCF (15 ng/mL), or Flt3 ligand (75 ng/mL) (see, e.g., Xu et al., (2005) *Stem Cells* 23(3):315). These media formulations have the advantage of supporting cell growth at 2-3 times the rate in other systems (see, e.g., WO 03/020920). In some embodiments pPS cells such as hES cells may be cultured in a media comprising bFGF and TGFβ. Suitable concentrations of bFGF include about 80 ng/ml. Suitable concentrations of TGFβ include about 0.5 ng/ml.

In some embodiments, the primate pluripotent stem cells may be plated at >15,000 cells $cm^{-2}$ (optimally 90,000 $cm^{-2}$ to 170,000 $cm^{-2}$). Typically, enzymatic digestion may be halted before cells become completely dispersed (e.g., about 5 minutes with collagenase IV). Clumps of about 10 to about 2,000 cells may then be plated directly onto a suitable substrate without further dispersal. Alternatively, the cells may be harvested without enzymes before the plate reaches confluence by incubating the cells for about 5 minutes in a solution of 0.5 mM EDTA in PBS or by simply detaching the desired cells from the plate mechanically, such as by scraping or isolation with a fine pipette or a cell scraper. After washing from the culture vessel, the cells may be plated into a new culture without further dispersal. In a further illustration, confluent human embryonic stem cells cultured in the absence of feeders may be removed from the plates by incubating with a solution of 0.05% (wt/vol) trypsin (Gibco®, Carlsbad, Calif.) and 0.05 mM EDTA for 5-15 minutes at 37° C. The remaining cells in the plate may be removed and the cells may be triturated into a suspension comprising single cells and small clusters, and then plated at densities of 50,000-200,000 cells $cm^{-2}$ to promote survival and limit differentiation.

In certain embodiments, pPS cells may be cultured on a layer of feeder cells, typically fibroblasts derived from embryonic or fetal tissue (Thomson et al. (1998) *Science* 282:1145). In certain embodiments, those feeder cells may be derived from human or murine source. Human feeder cells can be isolated from various human tissues or derived by differentiation of human embryonic stem cells into fibroblast cells (see, e.g., WO 01/51616) In certain embodiments, human feeder cells that may be used include, but are not limited to, placental fibroblasts (see, e.g., Genbacev et al. (2005) *Fertil. Steril.* 83(5):1517), fallopian tube epithelial cells (see, e.g., Richards et al. (2002) *Nat. Biotechnol.,* 20:933), foreskin fibroblasts (see, e.g., Amit et al. (2003) *Biol. Reprod.* 68:2150), uterine endometrial cells (see, e.g., Lee et al. (2005) *Biol. Reprod.* 72(1):42).

In the practice of the present invention, there are various solid surfaces that may be used in the culturing of cells. Those solid surfaces include, but are not limited to, standard commercially available cell culture plates such as 6-well, 24-well, 96-well, or 144-well plates. Other solid surfaces include, but are not limited to, microcarriers and disks. In certain embodiments, the microcarriers may be used in stirred-tank bioreactors for attachment of the cells. In certain embodiments, the microcarriers are beads. Those beads come in various forms such as Cytodex Dextran microcarrier beads with positive charge groups to augment cell attachment, gelatin/collagen-coated beads for cell attachment, and macroporous microcarrier beads with different porosities for attachment of cells. The Cytodex dextran, gelatin-coated and the macroporous microcarrier beads are commercially available (Sigma-Aldrich, St. Louis, Mo. or Solohill Engineering Inc., Ann Arbor, Mich.). In certain embodiments, the beads are 90-200 μm in size with an area of 350-500 $cm^2$. Beads may be composed of a variety of materials such as, but not limited to, glass or plastic. Disks are sold by companies such as New Brunswick Scientific Co, Inc. (Edison, N.J.). In certain embodiments, the disks are Fibra-cel Disks, which are polyester/polypropylene disks. A gram of these disks provide a surface area of 1200 $cm^2$.

The solid surface suitable for growing pPS cells may be made of a variety of substances including, but not limited to, glass or plastic such as polystyrene, polyvinylchloride, polycarbonate, polytetrafluorethylene, melinex, or thermanox. In certain embodiments of the invention, the solid surfaces may be three-dimensional in shape. Exemplary three-dimensional solid surfaces are described, e.g., in US 2005/0031598.

In certain embodiments, the cells are in a single-cell suspension during the methods of the invention. The single-cell suspension may be performed in various ways including, but not limited to, culture in a spinner flask, in a shaker flask, or in a fermentors. Fermentors that may be used include, but are not limited to, Celligen Plus (New Brunswick Scientific Co, Inc., Edison, N.J.), and the STR or the Stirred-Tank Reactor (Applikon Inc., Foster City, Calif.). In certain embodiments, the bioreactors may be continuously perfused with media or used in a fed-batch mode. Other suitable bioreactors include the Wave Bioreactor bags (GE Healthcare, Piscataway, N.J.). Bioreactors come in different sizes including, but not limited to 2.2 liter, 5 liter, 7.5 liter, 14 liter or 20 liter, 100 liter, 100 liter, 10,000 liter or larger.

General Techniques

For further elaboration of general techniques useful in the practice of this invention, the practitioner can refer to standard textbooks and reviews in cell biology, tissue culture, embryology, developmental biology, immunology, neurobiology, endocrinology, cardiology and the like.

With respect to tissue and cell culture and embryonic stem cells, the reader may wish to refer to any of numerous publications available in the art, e.g., *Teratocarcinomas and Embryonic Stem cells: A Practical Approach* (E. J. Robertson, Ed., IRL Press Ltd. 1987); *Guide to Techniques in Mouse Development* (P. M. Wasserman et al., Eds., Academic Press 1993); Embryonic Stem Cell Differentiation in Vitro (M. V. Wiles, Meth. Enzymol. 225:900, 1993); *Properties and Uses of Embryonic Stem Cells: Prospects for Application to Human Biology and Gene Therapy* (P. D. Rathjen et al., Reprod. Fertil. Dev. 10:31, 1998; and R. I. Freshney, Culture of Animal Cells, Wiley-Liss, New York, 2000).

Where derived from an established line of pPS cells, the cell populations and isolated cells of this invention can be characterized as having the same genome as the line from which they are derived. This means that the chromosomal DNA will be essentially identical by RFLP or by SNP analysis between the pPS cells and the differentiated progeny cells (assuming the cells have not been genetically manipulated by the human hand). It is contemplated that relatively minute changes in the genome may occur over time, e.g. in the non-coding regions, however overall the genetic identity will be substantially maintained between the parent cell line and any progeny, e.g. differentiated progeny. Typically the level of genetic identity will be similar to genetic identity observed between identical twins.

Genetic Alteration of Differentiated Cells

The cells of this invention can be made to contain one or more genetic alterations by genetic engineering of the cells either before or after differentiation (US 2002/0168766 A1). For example in some embodiments, the cells can be processed to increase their replication potential by genetically altering the cells to express telomerase reverse transcriptase, either before or after they progress to restricted developmental lineage cells or terminally differentiated cells (US 2003/0022367 A1).

The cells of this invention can also be genetically altered in order to enhance their ability to be involved in modulating a specific therapeutic function, or to deliver a therapeutic gene to a site of administration. A vector is designed using the known encoding sequence for the desired gene, operatively linked to a promoter that is either active in all cell types or specifically active in the differentiated cell type. Alternatively the promoter may be an inducible promoter that permits for the timed expression of the genetic alteration. For example the cells may be genetically engineered to express a cytokine that modulates a cardiac function.

Additional Aspects of the Invention

Additional aspects of the invention include the following:
1. A method of reducing the number of extraneous phenotypic cells in a mixed population of cells comprising a) contacting the mixed population of cells with one or more ligands that specifically bind to the extraneous phenotypic cells; and b) separating the ligand bound extraneous phenotypic cells from the rest of the mixed population of cells thereby reducing the number of extraneous phenotypic cells from a mixed population of cells, wherein the mixed population of cells comprises the in vitro differentiated progeny of pPS cells including the extraneous phenotypic cells.
2. The method of 1, wherein the extraneous phenotypic cell is an epithelial cell.
3. The method of 2, wherein the epithelial cell expresses a cytokeratin.
4. The method of 2, wherein the epithelial cell expresses EpCAM.
5. The method of 4, wherein one or more of the cells expressing EpCAM also expresses TRA-1-60.
6. The method of 1, wherein the ligand is an antibody.
7. The method of 6, wherein the antibody binds specifically to EpCAM.
8. The method of 1, wherein the ligand is bound to a solid support.
9. The method of 8, wherein the solid support is a bead.
10. The method of 9, wherein the bead is a magnetic bead.
11. The method of claim 1, wherein separating the ligand bound extraneous phenotypic cells from the rest of the mixed population of cells is performed by applying an external force to the mixed population of cells.
12. The method of 11, wherein the external force is provided by a magnetic field.
13. The method of 1, wherein the mixed population of cells comprises a targeted phenotype.
14. The method of 13, wherein the targeted phenotype is chosen from an oligodendrocyte, a cardiomyocyte, an islet cell, a hematopoietic cell, a hepatocyte, an osteoblast and a chondrocyte.
15. The method of 14 wherein the targeted phenotype is an oligodendrocyte.
16. The method of 14, wherein the targeted phenotype is a cardiomyocyte.
17. A method of reducing the number of extraneous phenotypic cells in a mixed population of cells comprising a) contacting the mixed population of cells with one or more ligands that specifically bind to one or more markers expressed by an epithelial cell; and b) separating the ligand bound cells of a) from the rest of the mixed population of cells thereby reducing the number of extraneous phenotypic cells from a mixed population of cells, wherein the mixed population of cells comprises the in vitro differentiated progeny of pPS cells including the extraneous phenotypic cells.
18. The method of 17, wherein the marker expressed by the epithelial cell is a cytokeratin.
19. The method of 17, wherein the marker expressed by the epithelial cell is EpCAM.
20. The method of 19, wherein the cells expressing EpCAM also expresses TRA-1-60.
21. The method of 17, wherein the ligand is an antibody.
22. The method of 21, wherein the antibody binds specifically to EpCAM.
23. The method of 17, wherein the ligand is bound to a solid support.
24. The method of 17, wherein the solid support is a bead.
25. The method of 24, wherein the bead is a magnetic bead.
26. The method of 17, wherein separating the ligand bound extraneous phenotypic cells from the rest of the mixed population of cells is performed by applying an external force to the mixed population of cells.
27. The method of 26, wherein the external force is provided by a magnetic field.
28. The method of 17, wherein the mixed population of cells comprises a targeted phenotype.
29. The method of 28, wherein the targeted phenotype is chosen from an oligodendrocyte, a cardiomyocyte, an islet cell, a hematopoietic cell, a hepatocyte, an osteoblast and a chondrocyte.
30. The method of 28, wherein the targeted phenotype is an oligodendrocyte.
31. The method of 28, wherein the targeted phenotype is a cardiomyocyte.
32. A method of reducing the number of extraneous phenotypic cells in a mixed population of cells comprising a) contacting the mixed population of cells with one or more ligands that specifically bind epithelial cells and contacting the mixed population of cells with one or more ligands that specifically bind to undifferentiated pPS cells; and b) separating the ligand bound cells from the rest of the mixed population of cells thereby reducing the number of extraneous phenotypic cells from a mixed population of cells, wherein the mixed population of cells comprises the in vitro differentiated progeny of pPS cells.
33. The method of 32, wherein the marker expressed by the epithelial cell is a cytokeratin.
34. The method of 32, wherein the marker expressed by the epithelial cell is EpCAM.
35. The method of 34, wherein the cells expressing EpCAM also express TRA-1-60.
36. The method of 32, wherein the ligand is an antibody.
37. The method of 36, wherein the antibody binds specifically to EpCAM.
38. The method of 36, wherein the ligand is bound to a solid support.
39. The method of 38, wherein the solid support is a bead.
40. The method of 39, wherein the bead is a magnetic bead.

41. The method of 32, wherein separating the ligand bound extraneous phenotypic cells from the rest of the mixed population of cells is performed by applying an external force to the mixed population of cells.
42. The method of 41, wherein the external force is provided by a magnetic field.
43. The method of 32, wherein the mixed population of cells comprises a targeted phenotype.
44. The method of 43, wherein the targeted phenotype is chosen from an oligodendrocyte, a cardiomyocyte, an islet cell, a hematopoietic cell, a hepatocyte, an osteoblast and a chondrocyte.
45. The method of 43, wherein the targeted phenotype is an oligodendrocyte.
46. The method of 43, wherein the targeted phenotype is a cardiomyocyte.
47. The method of 32, wherein the ligand that binds to the undifferentiated pPS cell is an antibody.
48. The method of 47, wherein the antibody binds to TRA-1-60.
49. The method of 48, wherein the antibody that binds to TRA-1-60 is an IgG.
50. The method of 48, wherein the antibody that binds to TRA-1-60 is an IgM
51. The method of 32, wherein the ligand that binds to an extraneous phenotypic cell is an antibody that specifically binds to EpCAM and the ligand that binds to an undifferentiated pPS cell is an antibody that binds to TRA-1-60.
52. The method of 51, wherein the antibody that binds to EpCAM is linked to a magnetic bead and the antibody that binds to TRA-1-60 is linked to a magnetic bead.
53. A method of reducing the number of extraneous phenotypic cells in a mixed population of cells comprising a) contacting the mixed population of cells with one or more ligands that specifically bind to EpCAM and b) separating the EpCAM bound cells from the rest of the mixed population of cells thereby reducing the number of extraneous phenotypic cells from a mixed population of cells, wherein the mixed population of cells comprises the in vitro differentiated progeny of pPS cells.
54. The method of 53, wherein the ligand that binds EpCAM is an antibody.
55. The method of 54, wherein the EpCAM antibody is linked to a solid support.
56. The method of 55, wherein the solid support is a bead.
57. The method of 56, wherein the bead is a magnetic bead.
58. The method of 53, wherein separating the ligand bound extraneous phenotypic cells from the rest of the mixed population of cells is performed by applying an external force to the mixed population of cells.
59. The method of 58, wherein the external force is provided by a magnetic field.
60. The method of 53, wherein the mixed population of cells comprises a targeted phenotype.
61. The method of 60, wherein the targeted phenotype is chosen from an oligodendrocyte, a cardiomyocyte, an islet cell, a hematopoietic cell, a hepatocyte, an osteoblast and a chondrocyte.
62. The method of 43, wherein the targeted phenotype is an oligodendrocyte.
63. The method of 43, wherein the targeted phenotype is a cardiomyocyte.
64. A method of reducing the number of extraneous phenotypic cells in a mixed population of cells comprising a) contacting the mixed population of cells with one or more ligands that specifically bind to EpCAM and one or more ligands that specifically bind to TRA-1-60; and b) separating the cells bound to the ligand for EpCAM and the cells bound to the ligand of TRA-1-60 from the rest of the mixed population of cells thereby reducing the number of extraneous phenotypic cells from a mixed population of cells, wherein the mixed population of cells comprises the in vitro differentiated progeny of pPS cells.
65. The method of 64, wherein the ligand that binds EpCAM is an antibody.
66. The method of 64, wherein the ligand that binds EpCAM is linked to a solid support.
67. The method of 66, wherein the solid support is a bead.
68. The method of 67, wherein the bead is a magnetic bead.
69. The method of 64, wherein the ligand that binds TRA-1-60 is an antibody.
70. The method of 69, wherein the antibody is an IgG.
71. The method of 69, wherein the antibody is an IgM.
72. The method of 64, wherein the ligand that binds TRA-1-60 is linked to a solid support.
73. The method of 72, wherein the solid support is a bead.
74. The method of 73, wherein the bead is a magnetic bead.
75. The method of 64, wherein separating the ligand bound extraneous phenotypic cells from the rest of the mixed population of cells is performed by applying an external force to the mixed population of cells.
76. The method of 75, wherein the external force is provided by a magnetic field.
77. The method of 64, wherein the mixed population of cells comprises a targeted phenotype.
78. The method of 77, wherein the targeted phenotype is chosen from an oligodendrocyte, a cardiomyocyte, an islet cell, a hematopoietic cell, a hepatocyte, an osteoblast and a chondrocyte.
79. The method of 77, wherein the targeted phenotype is an oligodendrocyte.
80. The method of 77, wherein the targeted phenotype is a cardiomyocyte.
81. A method of reducing the number of clustered epithelial forming cells in a mixed population of cells comprising a) contacting the mixed population of cells with one or more ligands that specifically bind to EpCAM and b) separating the EpCAM bound cells from the rest of the mixed population of cells thereby reducing the number of clustered epithelial forming cells from a mixed population of cells, wherein the mixed population of cells comprises the in vitro differentiated progeny of pPS cells.
82. The method of 81, wherein the ligand that binds EpCAM is an antibody.
83. The method of 82, wherein the EpCAM antibody is linked to a solid support.
84. The method of 83, wherein the solid support is a bead.
85. The method of 84, wherein the bead is a magnetic bead.
86. The method of 81, wherein separating the ligand bound extraneous phenotypic cells from the rest of the mixed population of cells is performed by applying an external force to the mixed population of cells.
87. The method of 81, wherein the external force is provided by a magnetic field.
88. The method of 88, wherein the mixed population of cells comprises a targeted phenotype.
89. The method of 88, wherein the targeted phenotype is chosen from an oligodendrocyte, a cardiomyocyte, an islet cell, a hematopoietic cell, a hepatocyte, an osteoblast and a chondrocyte.
90. The method of 88, wherein the targeted phenotype is an oligodendrocyte.
91. The method of 88, wherein the targeted phenotype is a cardiomyocyte.

92. A method of reducing the number of cells expressing one or more molecules expressed by undifferentiated cells in a mixed population of cells comprising a) contacting the mixed population of cells with one or more ligands that specifically an epithelial cell; and b) separating the ligand bound cells of a) from the rest of the mixed population of cells thereby reducing the number of undifferentiated cells from a mixed population of cells, wherein the mixed population of cells comprises the in vitro differentiated progeny of pPS cells.

93. The method of 92, wherein the ligand is an antibody.

94. The method of 92, wherein the antibody specifically binds to EpCAM.

95. The method of 92, wherein the antibody specifically binds to a cytokeratin.

96. The method of 92, wherein the antibody is linked to a solid support

97. The method of 96, wherein the solid support is a bead.

98. The method of 97, wherein the bead is a magnetic bead.

99. The method of 92, wherein separating the ligand bound extraneous phenotypic cells from the rest of the mixed population of cells is performed by applying an external force to the mixed population of cells.

100. The method of 99, wherein the external force is provided by a magnetic field.

101. The method of 92, wherein the mixed population of cells comprises a targeted phenotype.

102. The method of 101, wherein the targeted phenotype is chosen from an oligodendrocyte, a cardiomyocyte, an islet cell, a hematopoietic cell, a hepatocyte, an osteoblast and a chondrocyte.

103. The method of 101, wherein the targeted phenotype is an oligodendrocyte.

104. The method of 101, wherein the targeted phenotype is a cardiomyocyte.

105. The method of 92 wherein the molecule expressed by an undifferentiated cell is TRA-1-60.

106. A method of reducing the number of cells expressing one or more molecules expressed by undifferentiated cells in a mixed population of cells comprising a) contacting the mixed population of cells with one or more ligands that specifically bind to EpCAM and b) separating the ligand bound EpCAM cells from the rest of the mixed population of cells thereby reducing the number of undifferentiated cells from a mixed population of cells, wherein the mixed population of cells comprises the in vitro differentiated progeny of pPS cells.

107. The method of 106, wherein the molecule expressed by the undifferentiated cell is TRA-1-60.

108. The method of 106, wherein the ligand that binds EpCAM is an antibody.

109. The method of 108, wherein the EpCAM antibody is linked to a solid support.

110. The method of 108, wherein the solid support is a bead.

111. The method of 110, wherein the bead is a magnetic bead.

112. The method of 106, wherein separating the ligand bound extraneous phenotypic cells from the rest of the mixed population of cells is performed by applying an external force to the mixed population of cells.

113. The method of 112, wherein the external force is provided by a magnetic field.

114. The method of 106, wherein the mixed population of cells comprises a targeted phenotype.

115. The method of 114, wherein the targeted phenotype is chosen from an oligodendrocyte, a cardiomyocyte, an islet cell, a hematopoietic cell, a hepatocyte, an osteoblast and a chondrocyte.

116. The method of 114, wherein the targeted phenotype is an oligodendrocyte.

117. The method of 114, wherein the targeted phenotype is a cardiomyocyte.

118. A method of reducing the number of cells expressing one or more molecules expressed by undifferentiated cells in a mixed population of cells comprising a) contacting the mixed population of cells with one or more ligands that specifically bind to EpCAM and one or more ligands that specifically bind to TRA-1-60 and b) separating the ligand bound cells from the rest of the mixed population of cells thereby reducing the number of undifferentiated cells from a mixed population of cells, wherein the mixed population of cells comprises the in vitro differentiated progeny of pPS cells.

119. The method of 118, wherein the ligand that binds EpCAM is an antibody.

120. The method of 119, wherein the ligand that binds EpCAM is linked to a solid support.

121. The method of 120, wherein the solid support is a bead.

122. The method of 121, wherein the bead is a magnetic bead.

123. The method of 118, wherein the ligand that binds TRA-1-60 is an antibody.

124. The method of 118, wherein the antibody is an IgG.

125. The method of 118, wherein the antibody is an IgM.

126. The method of 118, wherein the ligand that binds TRA-1-60 is linked to a solid support.

127. The method of 126, wherein the solid support is a bead.

128. The method of 127, wherein the bead is a magnetic bead.

129. The method of 118, wherein separating the ligand bound extraneous phenotypic cells from the rest of the mixed population of cells is performed by applying an external force to the mixed population of cells.

130. The method of 129, wherein the external force is provided by a magnetic field.

131. The method of 118, wherein the mixed population of cells comprises a targeted phenotype.

132. The method of 131, wherein the targeted phenotype is chosen from an oligodendrocyte, a cardiomyocyte, an islet cell, a hematopoietic cell, a hepatocyte, an osteoblast and a chondrocyte.

133. The method of 131, wherein the targeted phenotype is an oligodendrocyte.

134. The method of 131, wherein the targeted phenotype is a cardiomyocyte.

135. A method of obtaining a population of cells comprising the in vitro differentiated progeny of pPS cells that is essentially free of extraneous phenotypic cells comprising a) obtaining a population of cells comprising the in vitro differentiated progeny of pPS cells; b) contacting the cell population of a) with one or more ligands that bind to epithelial cells and c) removing the ligand bound cells of b) thereby obtaining a population of cells that is essentially free of extraneous phenotypic cells.

136. The method of 135, wherein the ligand that binds the epithelial cell is EpCAM.

137. The method of 135, wherein the ligand that binds EpCAM is an antibody.

138. The method of 135, wherein the ligand that binds EpCAM is linked to a solid support.

139. The method of 138, wherein the solid support is a bead.

140. The method of 139, wherein the bead is a magnetic bead.

141. The method of 135, wherein removing the ligand bound extraneous phenotypic cells from the rest of the mixed population of cells is performed by applying an external force to the mixed population of cells.

142. The method of 141, wherein the external force is provided by a magnetic field.

143. The method of 135, wherein the mixed population of cells comprises a targeted phenotype.

144. The method of 143, wherein the targeted phenotype is chosen from an oligodendrocyte, a cardiomyocyte, an islet cell, a hematopoietic cell, a hepatocyte, an osteoblast and a chondrocyte.

145. The method of 143, wherein the targeted phenotype is an oligodendrocyte.

145. The method of 143, wherein the targeted phenotype is a cardiomyocyte.

146. A mixed population of cells that is enriched for a targeted phenotype, wherein the mixed population of cells comprises the in vitro differentiated progeny of pPS cells and wherein the mixed population of cells has been depleted of at least one cell expressing a molecule found on an epithelial cell.

147. The mixed population of cells of 146, wherein the at least one cell expressing a molecule found on an epithelial cell expresses EpCAM.

148. The mixed population of cells of 143, wherein the targeted phenotype is chosen from an oligodendrocyte, a cardiomyocyte, an islet cell, a hematopoietic cell, a hepatocyte, an osteoblast and a chondrocyte.

149. The mixed population of cells of 146, wherein the targeted phenotype is an oligodendrocyte.

150. The mixed population of cells of 146, wherein the targeted phenotype is a cardiomyocyte.

151. A mixed population of cells that is enriched for a targeted phenotype, wherein the mixed population of cells comprises the in vitro differentiated progeny of pPS cells and wherein the mixed population of cells has been depleted of at least one cell expressing a molecule found on an epithelial cell and at least one cell expressing a molecule found on an undifferentiated pluripotent stem cell.

152. The mixed population of cells of 151, wherein the at least one cell expressing a molecule found on an epithelial cell expresses EpCAM.

153. The mixed population of cells of 151, wherein the targeted phenotype is chosen from an oligodendrocyte, a cardiomyocyte, an islet cell, a hematopoietic cell, a hepatocyte, an osteoblast and a chondrocyte.

154. The mixed population of cells of 151, wherein the targeted phenotype is an oligodendrocyte.

155. The mixed population of cells of 151, wherein the targeted phenotype is a cardiomyocyte.

156. The mixed population of cells of 151, wherein the at least one cell expressing a molecule found on an undifferentiated cell expresses TRA-1-60.

157. A mixed population of cells that is enriched for a targeted phenotype, wherein the mixed population of cells comprises the in vitro differentiated progeny of pPS cells and wherein the mixed population of cells has been depleted of at least one cell expressing EpCAM.

158. The mixed population of cells of 157, wherein the targeted phenotype is chosen from an oligodendrocyte, a cardiomyocyte, an islet cell, a hematopoietic cell, a hepatocyte, an osteoblast and a chondrocyte.

159. The mixed population of cells of 157, wherein the targeted phenotype is an oligodendrocyte.

160. The mixed population of cells of 157, wherein the targeted phenotype is a cardiomyocyte.

161. A mixed population of cells that is enriched for a targeted phenotype, wherein the mixed population of cells comprises the in vitro differentiated progeny of pPS cells and wherein the mixed population of cells has been depleted of at least one cell expressing a cytokeratin.

162. The mixed population of cells of 161, wherein the targeted phenotype is chosen from an oligodendrocyte, a cardiomyocyte, an islet cell, a hematopoietic cell, a hepatocyte, an osteoblast and a chondrocyte.

163. The mixed population of cells of 161, wherein the targeted phenotype is an oligodendrocyte.

164. The mixed population of cells of 161, wherein the targeted phenotype is a cardiomyocyte.

165. The mixed population of cells of 161, wherein the at least one cell expressing a cytokeratin also expresses EpCAM.

166. A mixed population of cells that is enriched for a targeted phenotype, wherein the mixed population of cells comprises the in vitro differentiated progeny of pPS cells and wherein the mixed population of cells has been depleted of at least one cell expressing a cytokeratin and at least one cell expressing a molecule found on an undifferentiated cell.

165. The mixed population of cells of 166, wherein the at least one cell expressing a cytokeratin also expresses EpCAM.

167. The mixed population of cells of 166, wherein the at least one cell expressing a molecule found on an undifferentiated cell expresses TRA-1-60.

168. The mixed population of cells of 166, wherein the targeted phenotype is chosen from an oligodendrocyte, a cardiomyocyte, an islet cell, a hematopoietic cell, a hepatocyte, an osteoblast and a chondrocyte.

169. The mixed population of cells of 166, wherein the targeted phenotype is an oligodendrocyte.

170. The mixed population of cells of claim 166, wherein the targeted phenotype is a cardiomyocyte.

171. A mixed population of cells that is enriched for a targeted phenotype, wherein the mixed population of cells comprises the in vitro differentiated progeny of pPS cells and wherein the mixed population of cells has been depleted of at least one cell expressing EpCAM and at least one cell expressing TRA-1-60.

172. The mixed population of cells of 171, wherein the targeted phenotype is chosen from an oligodendrocyte, a cardiomyocyte, an islet cell, a hematopoietic cell, a hepatocyte, an osteoblast and a chondrocyte.

173. The mixed population of cells of 171, wherein the targeted phenotype is an oligodendrocyte.

174. The mixed population of cells of 171, wherein the targeted phenotype is a cardiomyocyte.

175. A mixed population of cells that is enriched for a targeted phenotype, wherein the mixed population of cells comprises the in vitro differentiated progeny of pPS cells and wherein the mixed population of cells has been depleted of at least one cell expressing a cytokeratin and at least one cell expressing TRA-1-60.

176. The mixed population of cells of 175, wherein the at least one cell expressing a cytokeratin also expresses EpCAM.

177. The mixed population of cells of 175, wherein the targeted phenotype is chosen from an oligodendrocyte, a cardiomyocyte, an islet cell, a hematopoietic cell, a hepatocyte, an osteoblast and a chondrocyte.

178. The mixed population of cells of 175, wherein the targeted phenotype is an oligodendrocyte.

179. The mixed population of cells of 175, wherein the targeted phenotype is a cardiomyocyte.

181. A kit for depleting cells having an extraneous phenotype from a mixed population of cells comprising a) a ligand for one or more molecules expressed on an epithelial cell; b) a ligand for one or more molecules expressed on an undifferentiated cell; and c) one or more containers, wherein the mixed population of cells comprises the in vitro differentiated progeny of pPS cells.

182. A kit for depleting cells having an extraneous phenotype from a mixed population of cells comprising a ligand for EpCAM, a ligand for TRA-1-60 and one or more containers, wherein the mixed population of cells comprises the in vitro differentiated progeny of pPS cells.

In the following Examples all experiments utilizing human embryonic cells (hES) cells were performed using established publicly available hES cell lines.

EXAMPLES

Example 1

Epithelial Cell Markers Correlate with Extraneous Phenotypes in Oligodendrocytes Differentiated in vitro from Primate Pluripotent Stem Cells Total RNA was extracted, according to the manufacturer's instructions using a Qiagen RNAEasy Kit (Qiagen, Valencia Calif.) from oligodendroglial progenitor cells differentiated in vitro from human embryonic stem cells. Vials containing $7.5\times10^6$ oligodendroglial progenitor cells each were used. These vials originated from three lots that generated a high number of clustered epithelial structures (CES) in vivo, and three lots that had low levels of CES in vivo. RNA integrity was confirmed using the Agilent bioanalyzer, (Agilent, Santa Clara, Calif.) and all samples used had an RNA integrity number (RIN) above 9.8. The 3' IVT Express kit (Affymetrix, Santa Clara, Calif.) was used according to the manufacturer's instructions to generate cDNA from this RNA. Microarray analysis was performed according to the manufacturer's instructions with these cDNA samples using the Affymetrix U133+2.0 genome array (Affymetrix, Santa Clara, Calif.). This array is a comprehensive human genome expression array containing more than 54,000 probe sets. Genes with greater than a 2-fold difference in expression between these groups of high and low CES lots were examined further. Table 1 shows that increased expression of epithelial cell markers correlates with increased expression of CES in lots of GRNOPC1.

TABLE 1

| Gene ID | Full Name | Fold expression difference (3 High CES vs. 3 Low CES lots) |
|---|---|---|
| KRT19 | Keratin 19 | 3.3 |
| EPPK1 | Epiplakin 1 | 3.1 |
| | | 2.8 |
| DSG2 | Desmoglein 2 | 3.1 |
| | | 2.9 |
| DSC3 | Desmocollin 3 | 2.6 |
| | | 2.5 |
| EpCAM | Epithelial cell adhesion marker | 2.3 |

Example 2

Identification of Epithelial Structures in Rat Spinal Cords

Rats that were administered human oligodendroglial progenitor cells which were differentiated in vitro from hES cells on rare occasions developed clustered epithelial structures. FIG. 1 shows clustered epithelial structures stained with hematoxylin and eosin. The structures were identified as epithelial cells based on morphology.

To further characterize these clustered epithelial structures immunohistochemistry (IHC) was performed using antibodies to pan-cytokeratin or an antibody to EpCAM. The pan-cytokeratin antibodies (Millipore, Billerica, Mass.) were a mixture of two antibodies: anti-AE1 and anti-AE3. The AE1 antibody recognizes keratins CK10, CK14, CK15, and CK16 as well keratin CK19. The AE3 antibody recognizes keratins CK1, CK2, CK3, CK4, CK5 and CK6, as well as keratins CK7 and CK8. Keratin CKIO is expressed in squamous keratinzed skin and some gut cells. Keratin CK19 is expressed in secretory epithelia, most glands, pseudostratified epithelia, secretory gut and respiratory epithelia. Keratin CK8 typically co-expresses with keratin CK18 and is found in most glands, secretory gut, and most secretory epithelia.

The EpCAM antibody used was Ber-Ep4 (Invitrogen, Carlsbad, Calif.). EpCAM is expressed at the basolateral membrane of most epithelial tissues and epithelial lineage cells. It is not expressed in squamous epithelium. It may be transiently expressed in association with cellular proliferation.

Sections were examined using (IHC) with pan-cytokeratin antiserum to label epithelial cells. Slides were deparaffinized using xylenes and a decreasing sequential ethanol series. Antigen retrieval pretreatment consisted of incubating the slides with 4% pepsin in DPBS for 30 minutes at 37° C., followed by cooling to ambient temperature. Slides were rinsed in DPBS and incubated with blocking buffer (0.3% Triton X-100, 10% normal goat serum, 1% bovine serum albumin, 3% $H_2O_2$ in DPBS) for 1 hour at ambient temperature followed by incubation with primary antiserum raised against pan-cytokeratin diluted 1:400, (catalogue #mAB 3412 clone AE1/AE3) (Millipore, Billerica, Mass.) for 24 hours at ambient temperature. The sections were washed and incubated with biotinylated secondary antibody diluted 1:500, (catalogue #BA-1000) (Vector Laboratories, Burlingame, Calif.) for 1 hour at ambient temperature, washed and incubated with streptavidin-HRP diluted 1:1000 in DPBS (Vectastain Elite ABC kit, Vector Laboratories) for 1 hour at ambient temperature. Ni-DAB, (Vector Laboratories) was used for HRP visualization. Slides were dehydrated through an increasing sequential ethanol series, defatted in xylenes and coverslipped with Permount™ (Fisher Scientific, Hampton, N.H.). The slides were examined under a light microscope.

Sections were examined using IHC with EpCAM antiserum to label epithelial cells. Slides were deparaffinized using xylenes and a decreasing sequential ethanol series. Antigen retrieval pretreatment consisted of incubating the slides with 4% pepsin in DPBS for 30 minutes at 37° C., followed by cooling to ambient temperature. Slides were rinsed in DPBS and incubated with blocking buffer (0.3% Triton X-100, 10% normal goat serum, 1% bovine serum albumin, 3% $H_2O_2$ in DPBS) for 1 hour at ambient temperature followed by incubation with primary antiserum raised against EpCAM diluted 1:100, (Ber-EP4; catalogue #mAB84 clone; Dako; Carpinteria, Calif.) for 24 hours at ambient temperature. The sections were washed and incubated with biotinylated secondary antibody diluted 1:500, (catalogue #BA-1000) (Vector Laboratories, Burlingame, Calif.) for 1 hour at ambient temperature, washed and incubated with streptavidin-HRP diluted 1:1000 in DPBS (Vectastain Elite ABC kit, Vector Laboratories) for 1 hour at ambient temperature. Ni-DAB, (Vector Laboratories) was used for HRP visualization. Slides were dehydrated through an increasing sequential ethanol series, defatted in xylenes and coverslipped with Permount™ (Fisher Scientific, Hampton, N.H.). The slides were examined under a light microscope.

Figure 2:
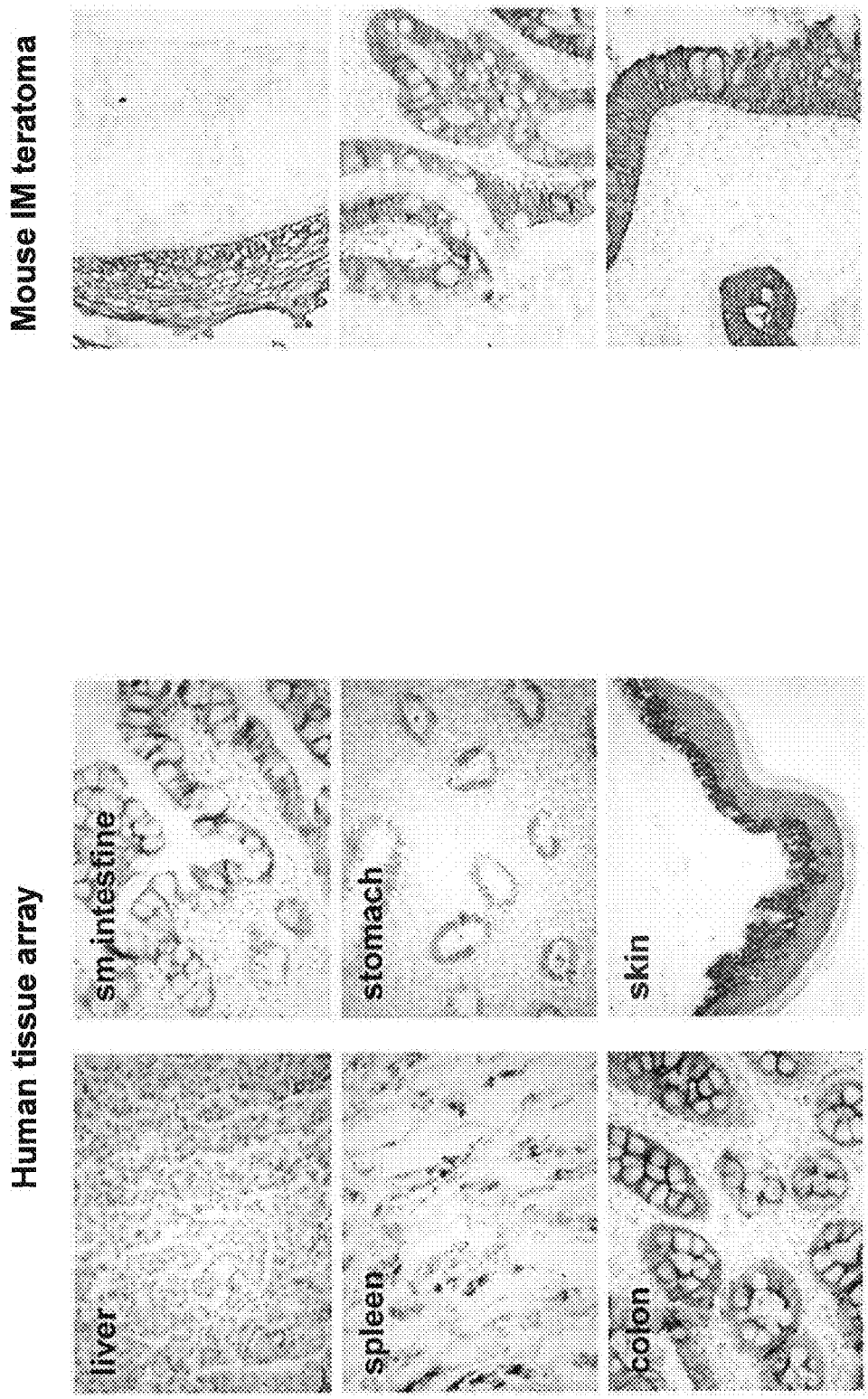
FIG. 2 is a series of photomicrographs showing that the pan-cytokeratin antibody AE1/AE3 labels a variety of tissue types found in a human tissue array (panels on left side) and also labels murine teratoma formed by injecting the mice intra-muscularly with undifferentiated hES cells (panels on right side).
Figure 3:
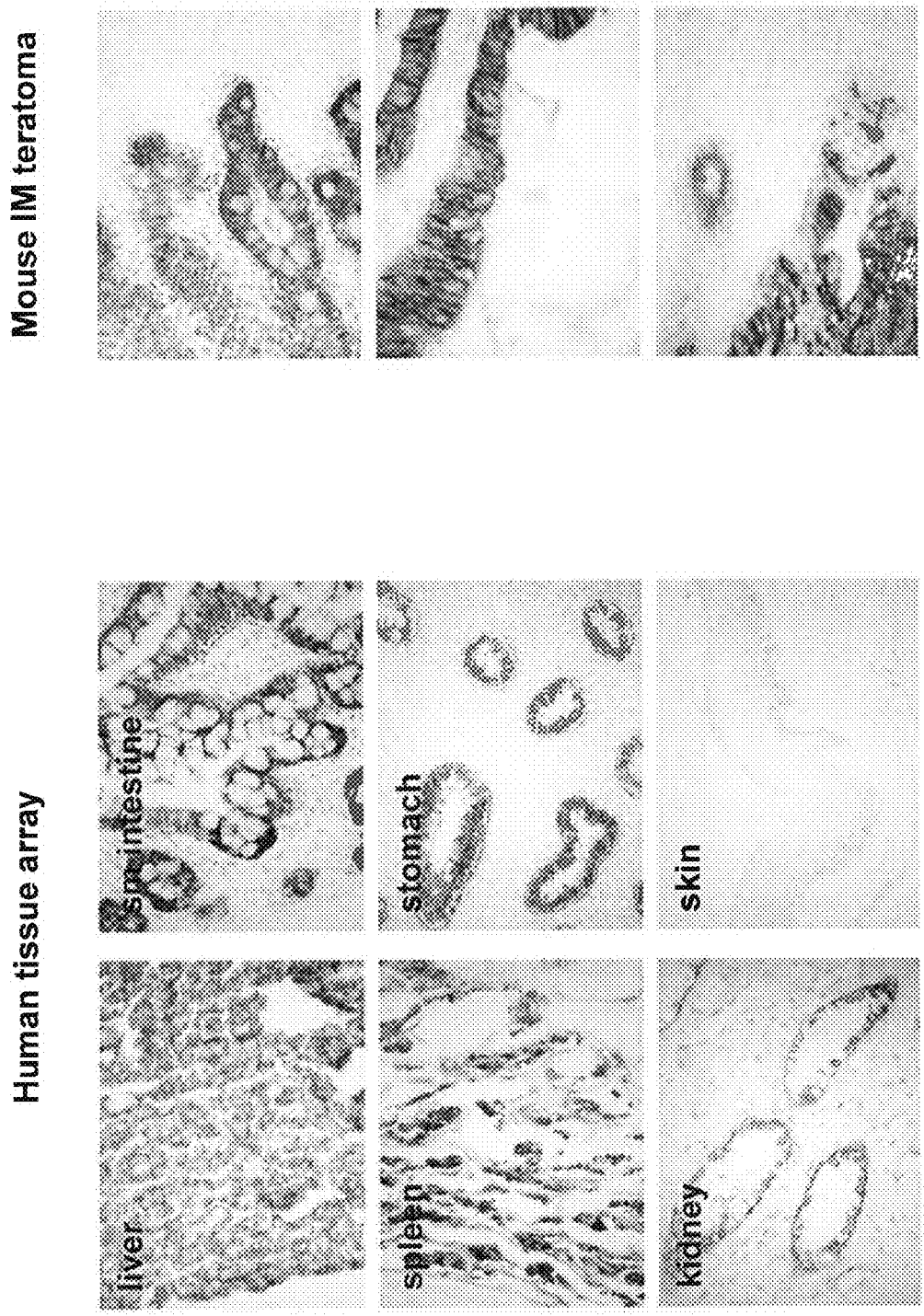
FIG. 3 are photomicrographs showing that the Ber-EP4 (EpCAM) antibody labels a variety of tissue types found in a human tissue array (panels on left side) and also labels murine teratomas formed by injecting the mice intra-muscularly with undifferentiated hES cells (panels on right side).

FIG. 2 demonstrates that human tissue array (containing liver, small intestine, spleen, stomach, colon and skin cells) all labeled for pan-cytokeratin. The right side of FIG. 2 demonstrates that murine intramuscular teratomas (in SKID/bg mice) also labeled for pan-cytokeratin. FIG. 3 shows similar results for the EpCAM antibody.

Figure 4:
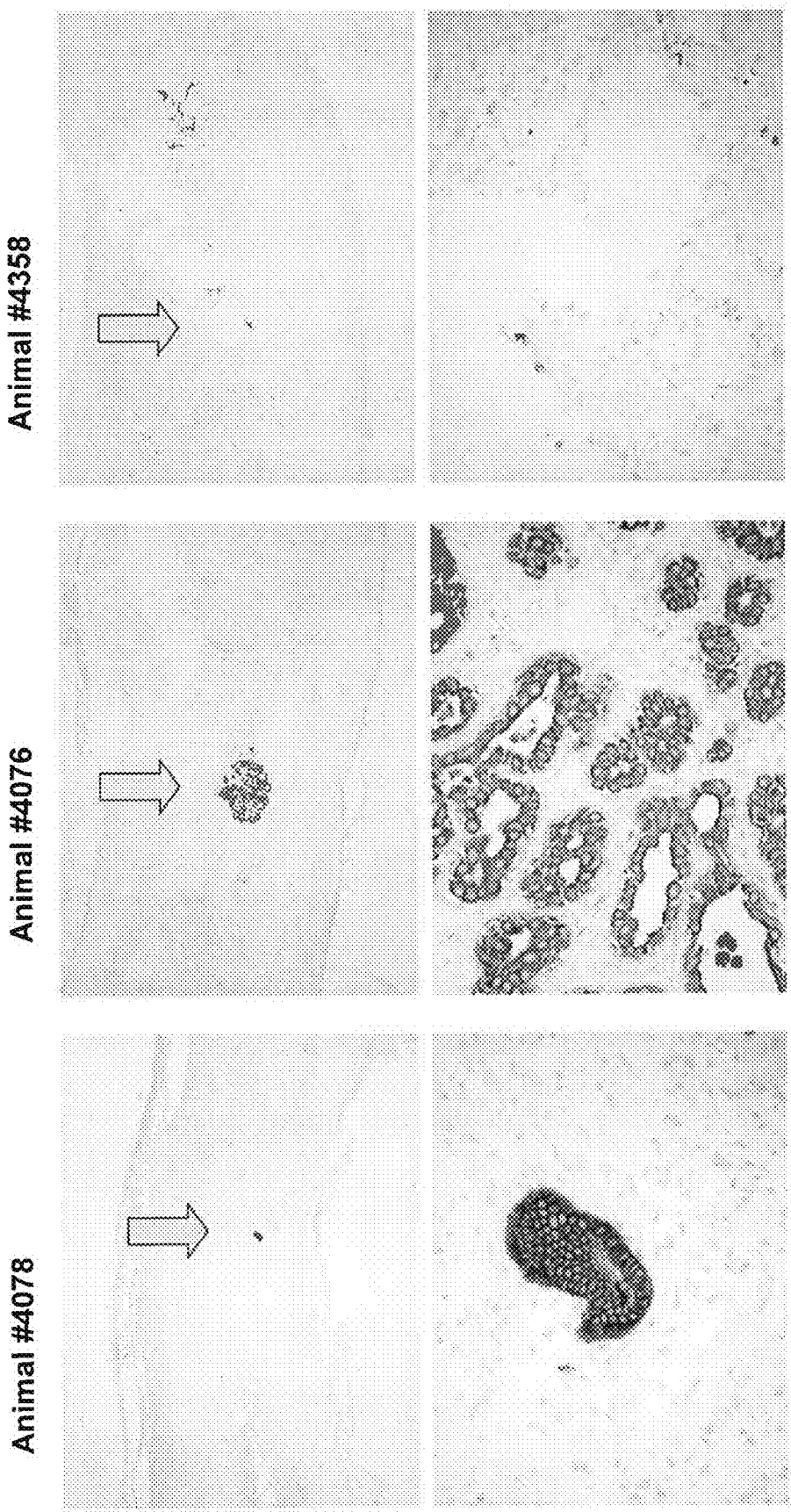
FIG. 4 is a series of photomicrographs showing clustered epithelial structures obtained from 3 rats administered a preparation of oligodendroglial progenitor cells differentiated in vitro from hES cells labeled positively in some cases with the pan-cytokeratin antibody AE1/AE3. Upper panel magnification is 24×. Lower panel magnification is 400×.
Figure 5:
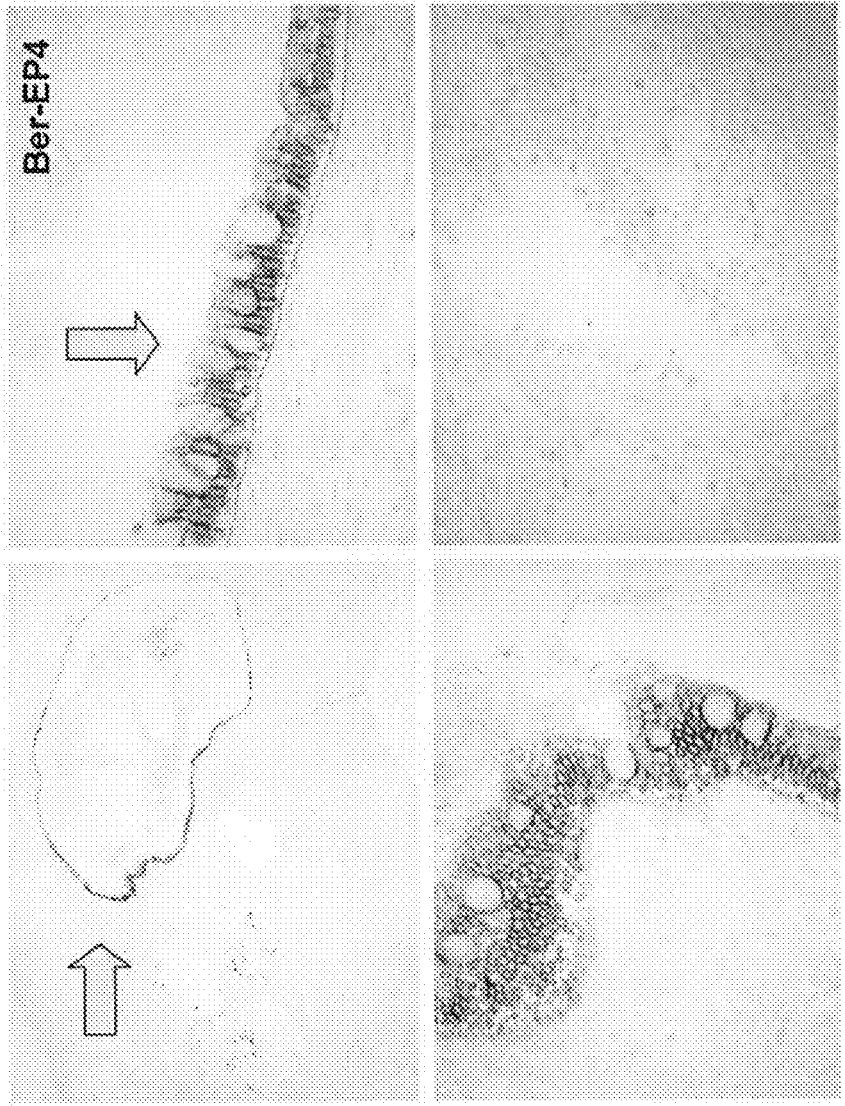
FIG. 5 is a series of photomicrographs showing clustered epithelial structures obtained from one rat administered a preparation of oligodendroglial progenitor cells differentiated in vitro from hES cells labeled in some cases with the Ber-EP4 EpCAM antibody.

FIG. 4 shows that the clustered epithelial structures in 3 distinct animals labeled positively for pan-cytokeratin. Magnifications shown are 24× (upper panels) and 400× (lower panels). FIG. 5 shows the clustered epithelial structure in one animal labeled with the EpCAM antibody. Magnifications shown are 24× (upper left panel) and 400× (lower panels).

Figure 6:
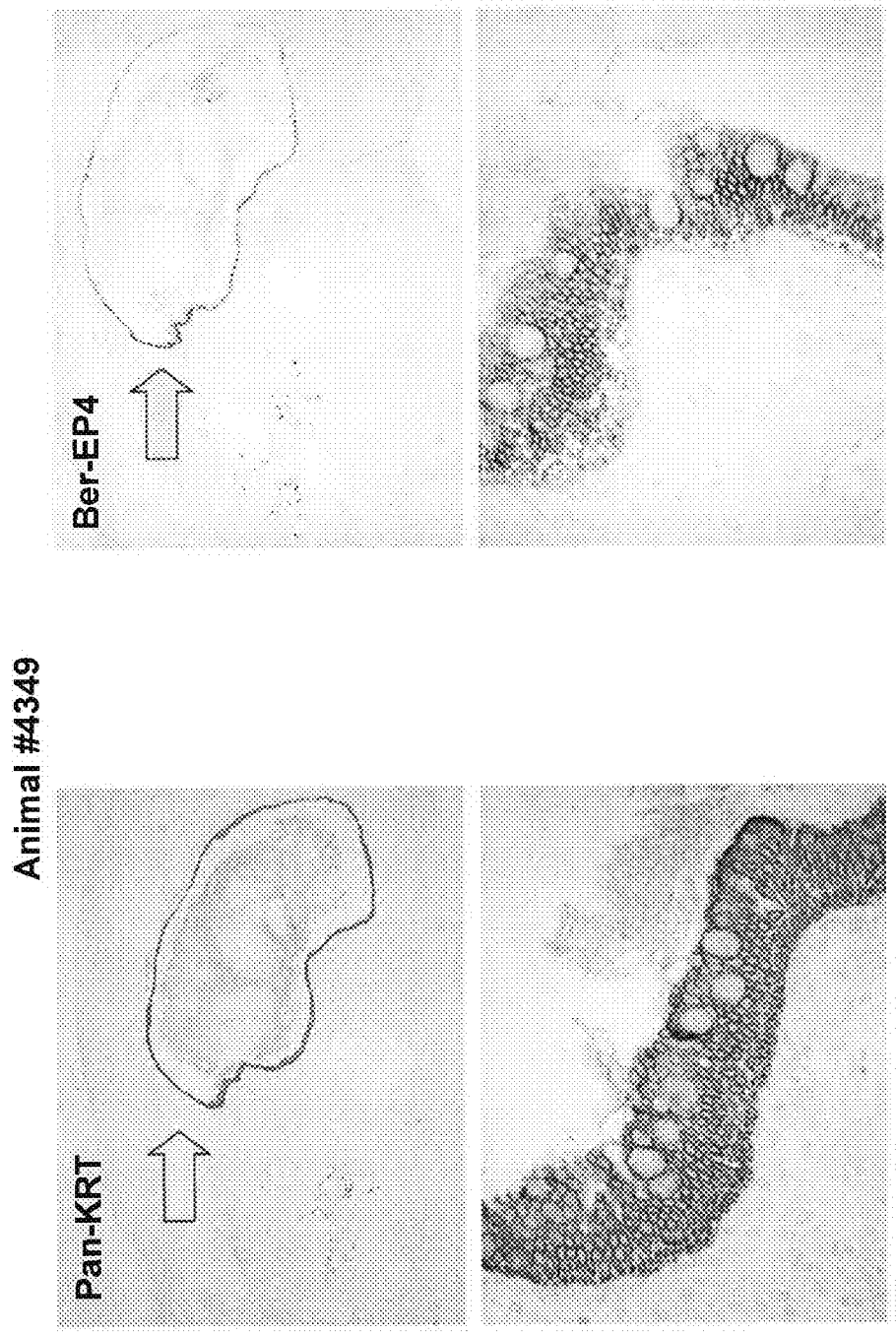
FIG. 6 is a series of photomicrographs showing clustered epithelial structures obtained from one rat administered a preparation of oligodendroglial progenitor cells differentiated in vitro from hES cells labeled in some cases with both the Ber-EP4 EpCAM antibody and the pan-cytokeratin antibody AE1/AE3.
Figure 7:
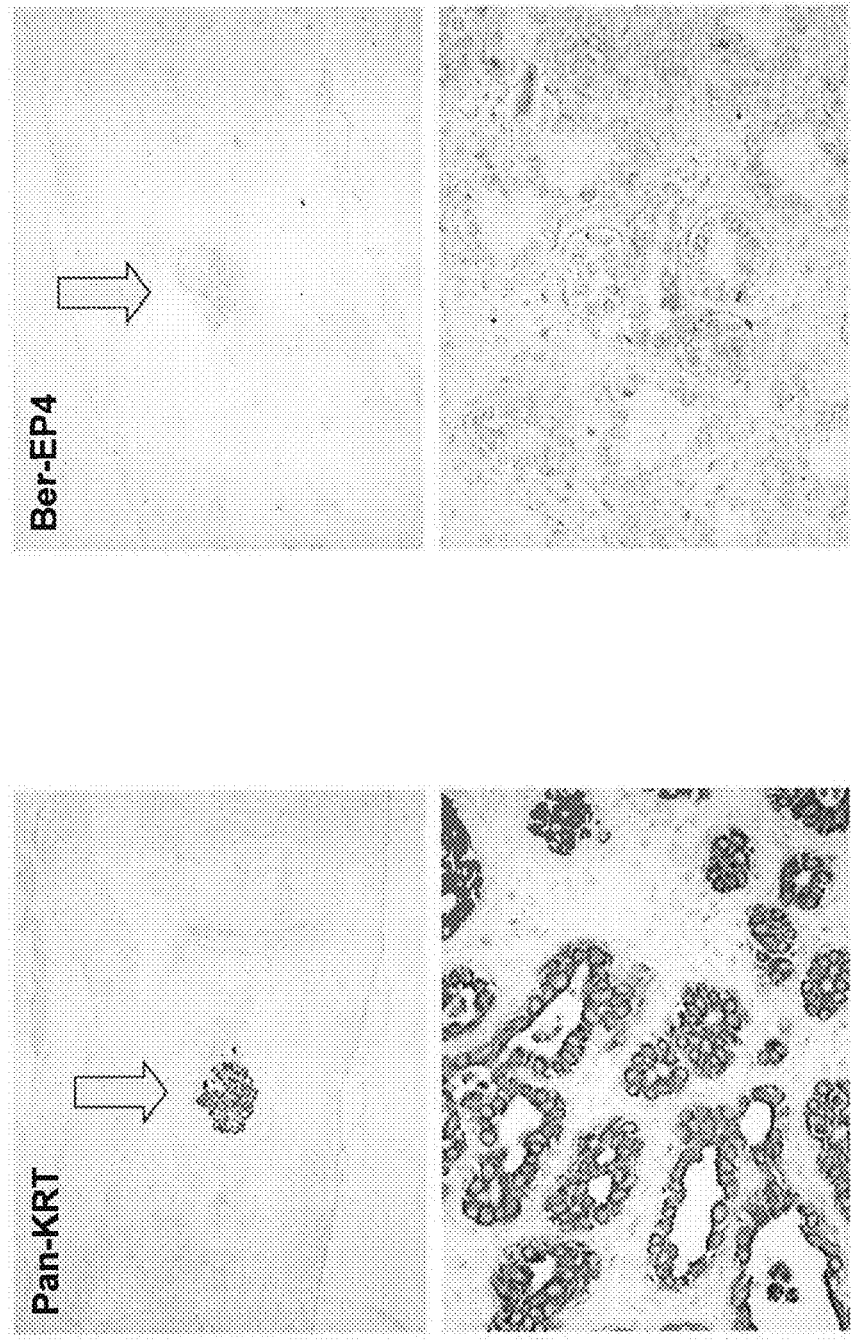
FIG. 7 is a series of photomicrographs showing clustered epithelial structures obtained from one rat administered a preparation of oligodendroglial progenitor cells differentiated in vitro from hES cells labeled in some cases with the pan-cytokeratin antibody AE1/AE3, but not the Ber-EP4 (EpCAM) antibody.
Figure 8:
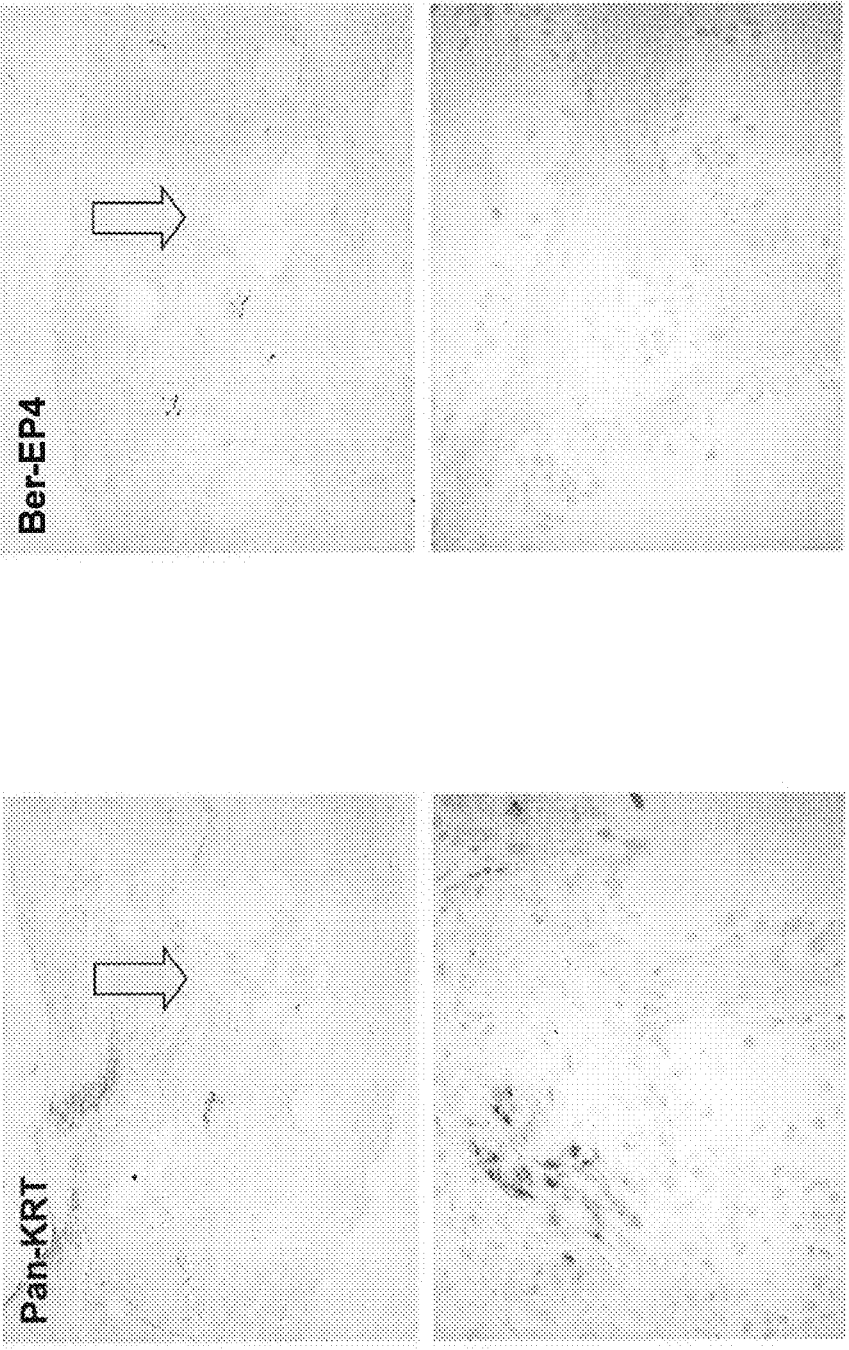
FIG. 8 is a series of photomicrographs showing clustered epithelial structures obtained from one rat administered a preparation of oligodendroglial progenitor cells differentiated in vitro from hES cells in which cells were labeled with neither the pan-cytokeratin antibody AE1/AE3, or the Ber-EP4 (EpCAM) antibody.

FIG. 6 shows the clustered epithelial structures in one animal labeled for both pan-cytokeratin and EpCam. Magnifications shown are 24× (upper panels) and 400× (lower panels). FIG. 7 shows that the clustered epithelial structures in one animal labeled for pan-cytokeratin, but not for EpCAM. Magnifications shown are 24× (upper panels) and 400× (lower panels). FIG. 8 shows that clustered epithelial structures in one animal did not label for either pan-cytokeratin or EpCAM. Magnifications shown are 24× (upper panels) and 400× (lower panels).

Example 3

Characterization of Mixed Populations of Cells Comprising Ollgodendrocytes hES cells were differentiated into oligodendrocytes and oligodendrocyte precursors as described above and in U.S. Pat. No. 7,285,415. Two separate lots (M07D1A and 2008-05A-ms) were generated. The cells in both preparations were characterized by flow cytometry by labeling the cells with antibodies for the following epithelial markers: EpCAM (clone BER-Ep4) conjugated to ALexa fluor 647 (Invitrogen, Carlsbad, Calif.) and a marker associated with primate undifferentiated pluripotent stem cells: TRA-1-60 (Invitrogen, Carlsbad, Calif.). The secondary antibody used for TRA-1-60 was an anti mouse IgM A488 conjugated with Alexa Fluor® (Invitrogen, Carlsbad, Calif.).

Figure 9:
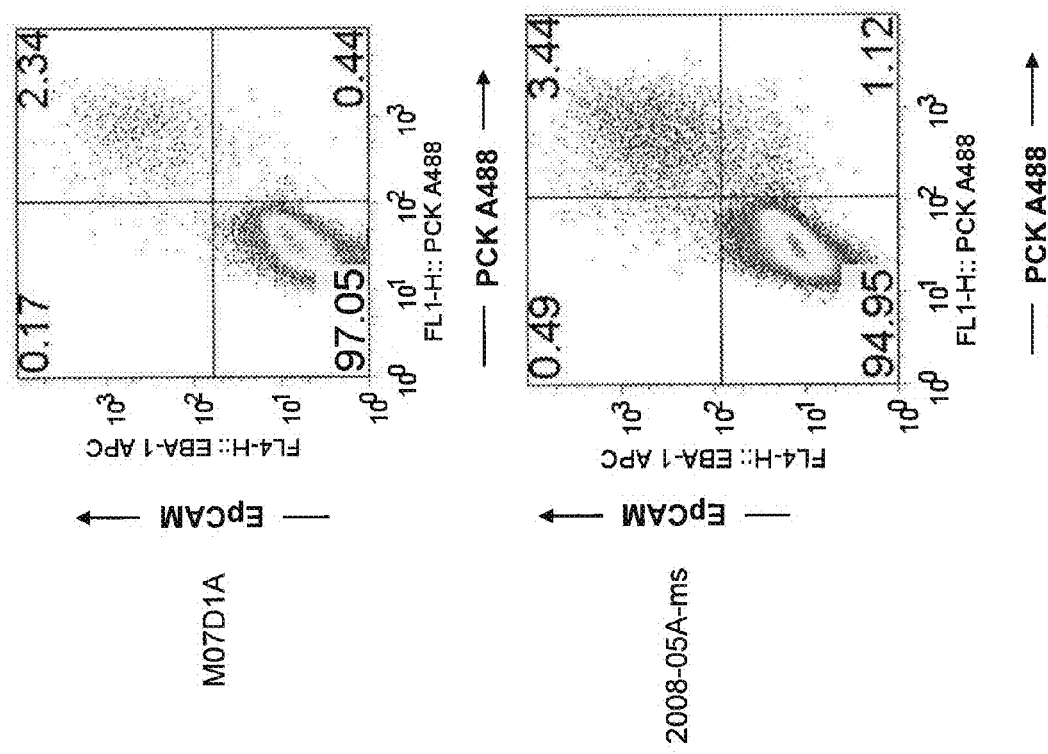
FIG. 9 shows data acquired by flow cytometry. Two different lots of oligodendroglial progenitor cells differentiated in vitro from human embryonic stem (hES) cells were labeled for EpCam, pan-cytokeratin and TRA-1-60.

Briefly, $5\times10^5$ cells were labeled per reaction in a volume of 100 μL. For primary antibodies 500 ng per label were used. The cells were incubated on ice for 15 minutes and then washed two times with staining buffer (0.5% Human serum albumin PBS). Secondary antibodies were diluted 1:400 and labeled on ice for 15 minutes. The cells were washed two times with staining buffer and then resuspended in propidium iodine staining buffer (prepared by adding 10 μL of a 1.0 mg/ml stock of propidium iodine to 2 ml of staining buffer for a final concentration of 5 μg/mL of propidium iodine). The cells were filtered using a FACS tube with a cell strainer (BD Bioscience, San Jose, Calif.). Cells were gated for propidium iodine vs. forward scatter and then again for forward scatter vs. side scatter. Within these gates 20,000 events were collected. The results are shown in FIG. 9 and indicate a small percentage of the population expressed pan-cytokeratin (both lots) and EpCAM (left panels). Most of the cells expressing EpCAM also labeled for pan-cytokeratin. Double positive cells are clearly evident.

Example 4

EpCAM Antibodies Successfully Remove EpCAM+ Cells from a Mixed Population of Cells In this experiment, an EpCAM negative cell line (Human Embryonic Kidney 293 cells) was spiked with EpCAM positive cell line (human adenocarcinoma line SW480) to create a mixed population that was 10% EpCAM+. The cells were labeled with the BER-Ep4 EpCAM antibody (Invitrogen, Carlsbad, Calif.) conjugated to a magnetic Dynal bead (CELLection Epithelial Enrich Bead) (Invitrogen, Carlsbad, Calif.) and the cells were separated using the Dynal CELLection kit (Invitrogen, Carlsbad, Calif.) according to the protocol below.

The Dynabeads (Invitrogen, Carlsbad, Calif.) were resuspended in the vial. 50 μL/2e7 cells of Dynabeads were transferred to a 15 mL tube. The same volume of Buffer 1 (PBS/ 0.1% Human Serum Albumin), or at least 1 mL was added to the tube and mixed. The tube was placed in the magnet for 1 minute and the supernatant was discarded. The tube was removed from the magnet and the washed. Dynabeads were resuspended in the same volume of Buffer 1 as the initial volume of Dynabeads.

To prepare the sample 2e7/mL cells were resuspended in cold Buffer 2 (PBS/0.1% Human Serum Albumin/2 mM EDTA). To enrich for EpCAM+ cells 50 μL of Dynabeads was added to 1 mL of prepared sample and then incubated for 30 minutes at 2-8° C. in MACSmix, (Invitrogen, Carlsbad, Calif.) set at gentle rotation. The tube was placed in the magnet for 2 minutes. The supernatant containing the EpCAM-depleted cells was reserved on ice.

The EpCAM+ bead-bound cells were washed 3× in preheated (37° C.) Buffer 3 (RPMI/0.1% HSA/1 mM $CaCl_2$/4 mM $MgCl_2$) (5 mL per wash) and placed in the magnet. All washes were pooled in a single tube. The cells were resuspended in 200 μL (per 2e7 cells) preheated (37° C.) Buffer 3. To release the EpCAM+ cells from the beads 4 μL of Releasing Buffer (DNAse) (provided in the kit) (Invitrogen, Carlsbad, Calif.) was added to the tube. The tube was incubated for 15 minutes at room temperature in a MACSmix, (Invitrogen, Carlsbad Calif.) set at gentle rotation. The contents of the tube were pipetted vigorously with a 1 mL pipette at least 5-10 times and then placed in the magnet for 2 minutes. The supernatant with released cells was transferred into a 15 mL tube pre coated with RPMI media. Samples were pooled. The beads were resuspended in Buffer 3 (200 μL) and the beads were once again pipetted vigorously and returned to the magnet for 2 minutes. The supernatant contained the unbound EpCAM+ cells.

Figure 10B:
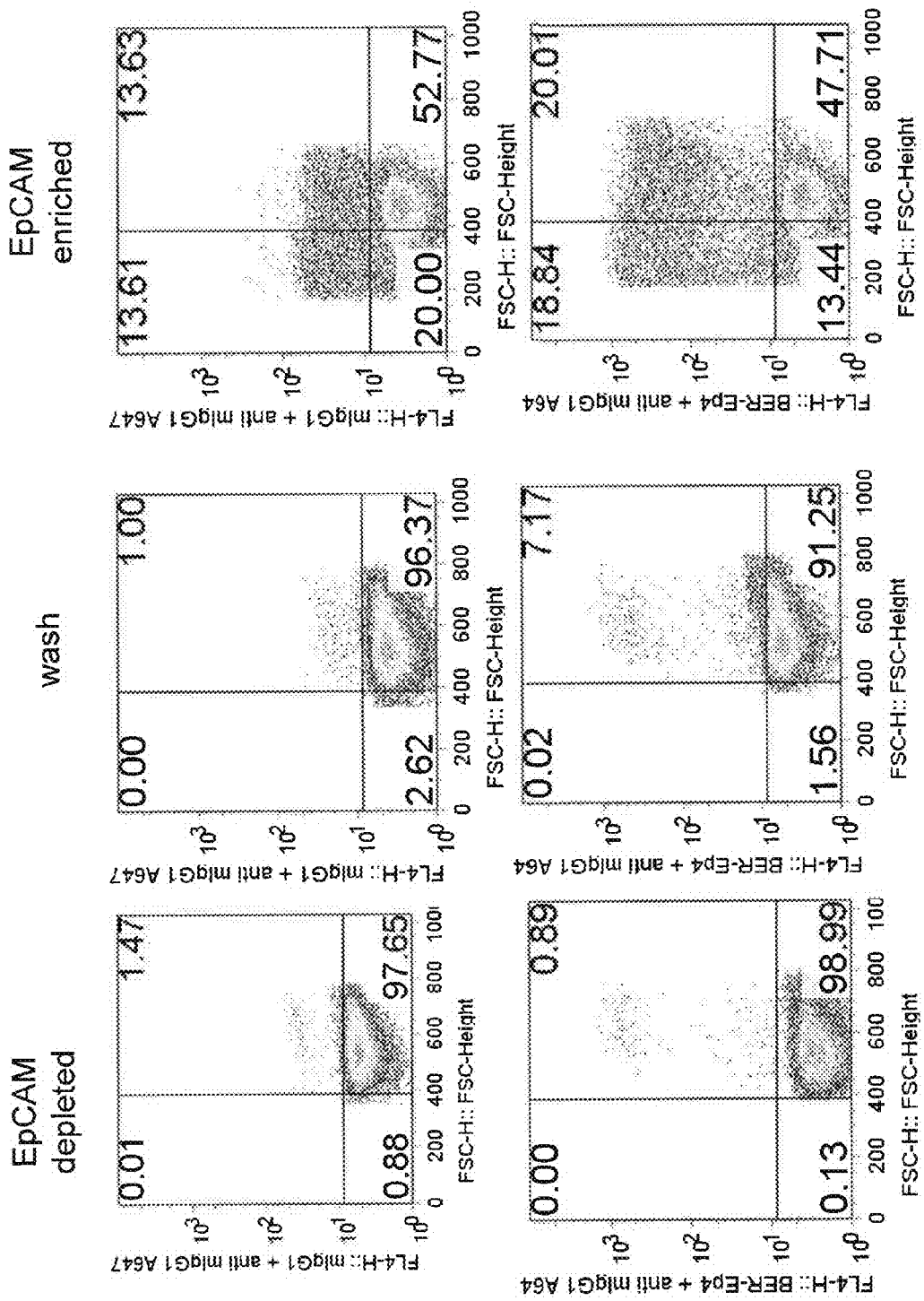
Figure 10C:
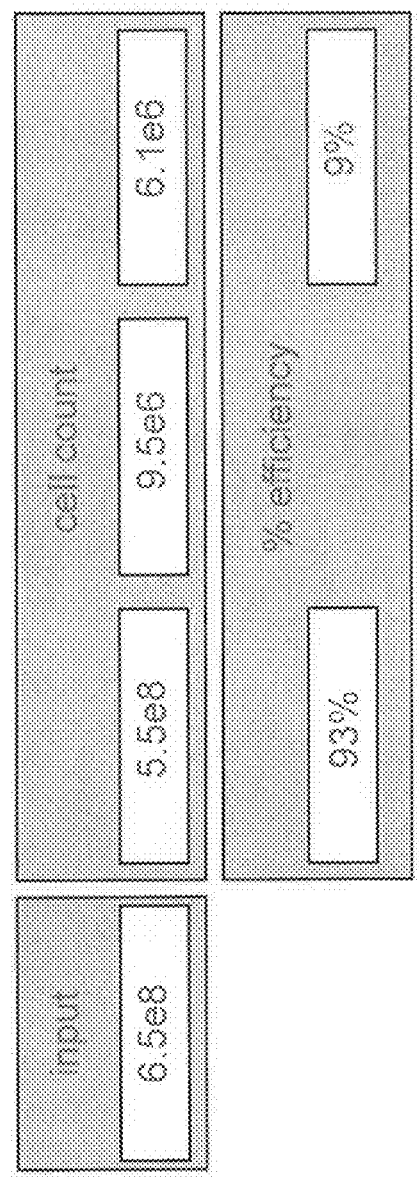

The cell fractions were labeled for EpCAM using the protocol described in Example 3. An isotype control (murine IgG1) (eBioscience, San Diego, Calif.) for the EpCAM antibody was used. The results are shown in FIG. 10A, FIG. 10B, and FIG. 10C. The data demonstrated that EpCAM+ cells could be successfully depleted from a mixed population of cells (see FIG. 10C bottom $3^{rd}$ and $4^{th}$ panel). Efficiency of recovery of the EpCAM negative cells was calculated to be 93%. Efficiency of recovery of the EpCAM positive cells was calculated to be 9%.

Example 5

Depleting EpCAM+ Cells Simultaneously Depletes Pan-Cytokeratin+ Cells and TRA-1-60 Cells In this experiment, anti-EpCAM Dynabeads (Invitrogen, Carlsbad, Calif.) were resuspended in the vial and 25 beads per target EpCAM expressing cell were transferred to a mL tube (assumed to be 5% of the target population-5% was chosen as an estimate of the number of EpCAM+ cells in the population. 5% is higher than the upper limit seen in previous populations of oligodendroglial progenitors differentiated in vitro from hES cells). The same volume of Buffer 1 (PBS/

0.1% Human Serum Albumin), or at least 1 mL was added to the tube and mixed in order to wash the beads prior to use. The tube was placed in the magnet for 1 minute and the supernatant was discarded. The tube was removed from the magnet and the washed. Dynabeads were resuspended in the same volume of Buffer 1 as the initial volume of Dynabeads.

To prepare the sample 2e7/mL cells (mixed population of cells comprising oligodendroglial progenitor cells differentiated in vitro from hES cells) were resuspended in cold Buffer 2 (PBS/0.1% Human Serum Albumin/2 mM EDTA). To deplete EpCAM+ cells the Dynabeads were added to the prepared sample and then incubated for 30 minutes at 2-8° C. in MACSmix, (Invitrogen, Carlsbad, Calif.) set at gentle rotation. The tube was placed in the magnet for 2 minutes. The supernatant containing the EpCAM-depleted cells was reserved on ice.

The cell fractions were labeled for EpCAM, TRA-1-60 and PCK using the protocol described in Example 3. Isotype controls (murine IgG1, murine IgM) (eBioscience, San Diego, Calif.) for the antibodies were used. The results are shown in FIG. 11. The data demonstrated that EpCAM+ cells could be successfully depleted from a mixed population of cells (see FIG. 11 bottom 3rd and 4th panel). Efficiency of recovery of the EpCAM negative cells was calculated to be 96%. In addition, EpCAM depletion reduced the percentages of both the TRA-1-60+ and PCK+ cell populations.

Example 6

EpCAM/TRA 1-60 Depleted Human Oligodendroglial Progenitor Cells Formed Fewer Epithelial Structures in Rat Spinal Cords This experiment investigated the effects of depletion of extraneous phenotypes on clustered epithelial formation in vivo using the rat as an animal model. Lots of human oligodendroglial progenitors expected to be high in clustered epithelial structures were chosen specifically for this study. Two groups of rats with spinal cord contusion injuries at the thoracic level received intraspinal cord injections of human oligodendroglial progenitor cells which either had, or had not been, depleted of EpCAM+/TRA 1-60+ cells. Six months later, animals were perfused and spinal cords were removed and sectioned on the longitudinal plane. The spinal cord tissue extending approximately 1 cm rostral and 1 cm caudal to the area of injury was stained with hematoxylin and eosin and examined for clustered epithelial structures. Results are shown in Table 2.

TABLE 2

Frequency of Epithelial Structure Formation Following Depletion of EpCAM+/TRA 1-60+ Cells

| Cell Type | Number of Animals with Epithelial Structures | Percent of Animals with Epithelial Structures |
|---|---|---|
| Oligodendroglial Progenitor Cells Differentiated in vitro from hES Cells | 6:10 | 60% |
| Oligodendroglial Progenitor Cells Differentiated in vitro from hES Cells Depleted of EpCAM+ Cells | 8:23 | 35% |

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

The invention claimed is:

1. A method of reducing the number of cells co-expressing TRA-1-60 and EpCAM in a mixed population of cells comprising:
   a) providing a mixed population of cells comprising the in vitro progeny of pPS cells, wherein the mixed population of cells comprises i) cells co-expressing TRA-1-60 and EpCAM, and ii) oligodendrocytes differentiated from the pPS cells;
   b) contacting the mixed population of cells with one or more ligands that specifically bind to EpCAM expressed on cells of the mixed population of cells; and
   c) separating the ligand bound EpCAM expressing cells from the rest of the mixed population of cells to thereby reduce the number of cells expressing TRA-1-60 in the mixed population of cells.

2. The method of claim 1, wherein the ligand is an antibody.

3. The method of claim 1, wherein the ligand is bound to a solid support.

4. The method of claim 3, wherein the solid support is a bead.

5. The method of claim 4, wherein the bead is a magnetic bead.

6. The method of claim 1, wherein separating the ligand bound EpCAM expressing cells from the rest of the mixed population of cells is performed by applying an external force to the mixed population of cells.

7. The method of claim 6, wherein the external force is provided by a magnetic field.

* * * * *